US008124351B2

(12) United States Patent
Albitar et al.

(10) Patent No.: US 8,124,351 B2
(45) Date of Patent: Feb. 28, 2012

(54) QUANTIFICATION OF FUSION PROTEINS AND THEIR ACTIVITY FROM CHROMOSOMAL TRANSLOCATION

(75) Inventors: Maher Albitar, Coto de Caza, CA (US); Hagop Kantarjian, Bellaire, TX (US); Francis Giles, Bellaire, TX (US); Iman Jilani, Houston, TX (US)

(73) Assignees: Board of Regents, The University of Texas System, Austin, TX (US); Quest Diagnostics Incorporated, San Clemente, CA (US)

( * ) Notice: Subject to any disclaimer, the term of this patent is extended or adjusted under 35 U.S.C. 154(b) by 450 days.

(21) Appl. No.: 12/094,112

(22) PCT Filed: Nov. 14, 2006

(86) PCT No.: PCT/US2006/044136
§ 371 (c)(1), (2), (4) Date: Mar. 9, 2009

(87) PCT Pub. No.: WO2007/061684
PCT Pub. Date: May 31, 2007

(65) Prior Publication Data
US 2009/0226933 A1  Sep. 10, 2009

Related U.S. Application Data

(60) Provisional application No. 60/738,141, filed on Nov. 18, 2005.

(51) Int. Cl.
*G01N 33/53* (2006.01)

(52) U.S. Cl. .......................................................... 435/7.1
(58) Field of Classification Search .......................... None
See application file for complete search history.

(56) References Cited

U.S. PATENT DOCUMENTS 6,414,133 B1  7/2002  Dietz-Band et al. ......... 536/24.3
(Continued)

FOREIGN PATENT DOCUMENTS

WO  WO 94/26930  11/1994
(Continued)

OTHER PUBLICATIONS

Tockman et al (Cancer Res., 1992, 52:2711s-2718s).*
(Continued)

*Primary Examiner* — Sean Aeder
(74) *Attorney, Agent, or Firm* — Fulbright & Jaworski L.L.P.

(57) ABSTRACT

The present invention concerns the detection of gene products resulting from chromosomal translocations, including fusion proteins comprising a first and second region. In particular, the fusion proteins are identified following subjecting a sample comprising the proteins to a bead comprising an antibody to a first region, followed by subjecting the bead-antibody-fusion complex to a second antibody directed against the second region, thereby detecting the fusion protein. In particular aspects, the invention is employed to provide prognosis for an individual with cancer, to identify suitability for a particular cancer therapy, and/or to monitor response of a patient to a therapy, for example.

18 Claims, 16 Drawing Sheets

U.S. PATENT DOCUMENTS

| | | | |
|---|---|---|---|
| 6,576,421 | B1 | 6/2003 | Westbrook .......................... 435/6 |
| 6,610,498 | B1 | 8/2003 | Berendes et al. .............. 435/7.1 |
| 6,686,165 | B2 | 2/2004 | van Dongen et al. .......... 435/7.1 |
| 2002/0042056 | A1 | 4/2002 | van Dongen et al. |
| 2002/0177130 | A1 | 11/2002 | Gray et al. ......................... 435/6 |
| 2003/0099987 | A1 | 5/2003 | Westbrook ......................... 435/6 |
| 2003/0190688 | A1 | 10/2003 | Crosby et al. |
| 2004/0203011 | A1 | 10/2004 | Morris et al. ..................... 435/6 |
| 2004/0235039 | A1 | 11/2004 | Gray et al. ......................... 435/6 |
| 2005/0214301 | A1 | 9/2005 | Wetzel et al. |

FOREIGN PATENT DOCUMENTS

| | | |
|---|---|---|
| WO | WO 95/15331 | 6/1995 |
| WO | WO 00/21975 | 4/2000 |
| WO | WO 03/087760 A2 * | 10/2003 |
| WO | WO 2004/016317 | 2/2004 |
| WO | WO-2004 042398 | 5/2004 |
| WO | WO 2007/061684 | 5/2007 |

OTHER PUBLICATIONS

Database Biosis, Bioscience Information Service, Philadelphia, PA, US; Nov. 2005. Jilani I et al., "Measurement of free circulating brc-abl fusion protein and its pbosphorylation in patients with chronic myeloid leukemia," XP002425944 Database Accession No. PREV200600184376 abstract & Blood, vol. 106(11) Part 1, Nov. 2005, p. 568A, 47th Annual Meeting of the American-Society-of-Hematology; Atlanta, GA, USA; Dec. 10-13, 2005. ISSN: 0006-4971.
International Preliminary Report on Patentability issued May 20, 2008, during the prosecution of International Application No. PCT/US2006/044136.
International Search Report issued Oct. 4, 2007, during the prosecution of International Application No. PCT/US2006/044136.
Written Opinion issued Oct. 4, 2007, during the prosecution of International Application No. PCT/US2006/044136.
"LightCycler-t(8;21) Quantification Kit and LightCycler-inv(16) Quantification Kit," *Biochemica*, 4:13-14, 2001.
"Monoclonal antibodies detecting human antigens," Immunocytometry Systems: Cytometry Source Book, accessed on www.fujisawa.co.jp/reagent/source/html/23_1909.htm, Aug. 27, 2003.
"Mouse anti-CD10," copyright: Zymed Laboratories 2002.
Ahmed et al., "Evaluation of some tissue and serum biomarkers in prostatic carcinoma among Egyptian males," *Clinical Biochemistry*, 32:439-445, 1999.
Ahuja et al., "The t(11;20) (p15;q11) chromosomal translocation associated with therapy-related myelodysplastic syndrome results in an *NUP98-TOP1* fusion," *Blood*, 9:3258-3261, 1999.
Avet-Loiseau et al., "Detection of t(11;14) using interphase molecular cytogenics in mantle cell lymphoma and atypical chronic lymphocytic leukemia," *Genes, Chromosomes, and Cancer*, 23:175-182, 1998.
Bégueret et al., "Primary intrathoracic synovial sarcoma: A clinopathologic study of 40t(x; 18) positive cases from the French sarcoma group and mesopath group," *Am. J. Surg. Pathol.*, 29(3):339-346, 2005.
Bourgeois et al., "Molecular detection of the *ETV6-NTRK3* gene fusion differentiates congenital fibrosarcoma from other childhood spindle cell tumors," *American Journal of Surgical Pathology*, 24:937-946, 2000.
Chan et al., "Detection of chromosome translocations by bead-base flow cytometry," *Methods in Molecular Biology*, 378:167-174, 2007.
Cheung et al., "Detection of the PAX8-PPARγ fusion oncogene in both follicular thyroid carcinomas and adenomas," *J Clin Endocrinol Metab*, 88:354-357, 2003.
Cordell et al., "Detection of normal and chimeric nucleophosmin in human cells," *Blood*, 93:632-642, 1999.

Dos Santos et al., "Molecular mechanisms underlying human synovial sarcoma development," *Genes, Chromosomes, and Cancer*, 30:1-14, 2001.
Dyomin et al., "*MUC1* is activated in B-cell lymphoma by the t(1;14) (q21;q32) translocation and is rearranged and amplified in B-cell lymphoma subsets," *Blood*, 95: 2666-2671, 2000.
Erber et al., "Unique immunophenotype of acute promyelocytic leukaemia as defined by CD9 and CD68 antibodies," *British Journal of Haemotology*, 88:101-104, 1994.
Falini et al., "Immunocytochemila diagnosis of acute promyelocytic leukemia (M3) with the monoclonal antibody of PG-M3 (Anti-PML)," *Blood*, 90:4046-4053, 1997.
Finelli et al., "Detection of t(4;14) (p16.3, q32) chromosomal translocation in multiple myeloma by double-color fluorescent in situ hybridization," *Blood*, 94:724-732, 1999.
Fonseca et al., "Clinical significance of the translocation (11;14) (q13; q32) in multiple myeloma," *Leukemia and Lymphoma*, 35:599-605, 1999.
Jilani et al., "An immunological method for the detection of BCR-ABL fusion protein and monitoring its activation," *Leukemia Research*, 32:936-943, 2008.
Kalantarov et al., "Development of a fusion partner cell line for efficient production of a human monoclonal antibodies from peripheral blood lymphocytes," *Human Antibodies*, 11:85-96, 85-96, 2002.
Kirman et al, "Isolation of the native human monoclonal autoantibodies to breast cancer," *Hybridoma and Hybridomics*, 21: 405-413, 2002.
Klugbauer et al., "A novel type of *RET* rearrangement (PTC8) in childhood papillary thyroid carcinomas and characterization of the involved gene (*RFG8*)," *Cancer Research*, 60: 7028-7032, 2000.
Leal et al., "High sensitivity of chemiluminescent methodology for detection of clonal CDR3 sequences in patients with acute lymphoblastic leukemia," *Hematological Oncology*, 22:55-61, 2004.
Lorenzen et al., "Single-cell analysis of T-cell receptor-γ rearrangement in large cell anaplastic lymphoma," *Diagnostic Molecular Pathology*, 5: 10-19, 1996.
Mihara et al., "Detection of hypermethylation of the C-ABL genomic locus in the spleen of juvenile rats," *Biochemical and Biophysical Research Communications*, 154:1061-1066, 1988.
Mirzabekov, "3D gel-based biochips for disease diagnosis," accessed from www.crdf.org/events/bio2003_3d_gel_based-biochips.htm on Aug. 28, 2003.
Murphy et al., "Primary desmoplastic small round cell tumor of bone: report of a case with cytogenic confirmation," *Cancer Genetics and Cytogenetics*, 156:167-171, 2005.
Ott et al., "BCL-1 rearrangement and cyclin D1 protein expression in mantle cell lymphoma," *Journal of Pathology*, 179:238-242, 1996.
Pane et al., "Neutrophilic-chronic myeloid leukemia: a distinct disease with a specific molecular marker (*BCR/ABL* with C3/A2 junction)," *Blood*, 88:2410-2414, 1996.
Privitera et al., "Different molecular consequences of the 1;19 chromosomal translocation in childhood B-cell precursor acute lymphoblastic leukemia," *Blood*, 79:1781-1788, 1992.
Rabbitts et al., "Chromosomal translocation products engender new intracellular therapeutic technologies," *Nat Med*, 9:383-386, 2003.
Talpaz et al., "Autoantibodies to Abl and Bcr proteins," *Leukemia*, 14: 1661-1666, 2000.
Valk et al. "Molecular diagnostis of hematopoetic diseases," accessed on www.eur.nl/fgg/hema/nederlands/onderzoek/overige.html, Aug. 27, 2003.
Van Denderen et al, "Immunological characterization of the tumor-specific *bcr-abl* junction in Philadelphia chromosome-positive acute lymphoblastic leukemia," *Blood*, 76:136-141, 1990.
Vega et al, "Chromosomal translocation involved in non-hodgin lymphomas," *Arch Pathol Lab Med*, 127:1148-1160, 2003.
Wallace et al., "Barcode-All: accelerated and cost-effective genetic risk stratification in acute leukemia using spectrally addressable liquid bead microarrays," *Leukemia*, 17: 1404-1410, 2003.

\* cited by examiner

| Spearman Rank Order Correlations | | | | |
|---|---|---|---|---|
| MD pairwise deleted | | | | |
| | Valid | Spearman | | |
| | N | R | t(N-2) | p-level |
| BCR-ABL protein & Baseline PCR in cells | 54 | 0.339127 | 2.599527 | 0.012121773 |
| BCR-ABL protein & Baseline PCR in Plasma | 51 | 0.415394 | 3.196598 | 0.00243563 |
| Phospho-BCR-ABL(TH) & PCR Ratio in plasma | 51 | 0.366298 | 2.755606 | 0.008202584 |
| Phospho-BCR-ABL(Tyr) & PCR Ratio in plasma | 51 | 0.42648 | 3.300577 | 0.001804277 |
| Phospho-BCR-ABL(Tyr) & PCR Ratio in BM plasma | 51 | -0.378759 | -2.864748 | 0.006129863 |
| | | | | |
| BCR-ABL protein & PROMYEL | 23 | 0.401895 | 2.011295 | 0.057304591 |
| BCR-ABL & HEMO | 26 | -0.38193 | -2.024548 | 0.054178733 |
| p(TH)BCR-ABL & PROMYEL | 23 | 0.488162 | 2.563199 | 0.018115489 |
| p(TH)BCR-ABL & MONO | 25 | -0.384982 | -2.000501 | 0.057386871 |
| p(TH)BCR-ABL & HEMO | 26 | -0.449008 | -2.461792 | 0.021393355 |
| p(Tyr)BCR-ABL & PROMYEL | 23 | 0.45119 | 2.316842 | 0.030698555 |
| p(Tyr)BCR-ABL & LDH | 24 | 0.351304 | 1.75994 | 0.092317253 |
| p(Th)BCR-ABL ratio & PLATELET | 26 | 0.375107 | 1.982392 | 0.058996316 |
| p(Tyr)BCR-ABL ratio & METAMYEL | 23 | 0.361358 | 1.775958 | 0.090233423 |
| | | | | |
| BCR-ABL & PB3RESUL | 18 | 0.354777 | 1.51784 | 0.148564741 |
| BCR-ABL & DIF3_MON | 18 | -0.354777 | -1.51784 | 0.148564741 |
| BCR-ABL & PCR at 3 Month in Plasma,ABS | 13 | -0.543956 | -2.150004 | 0.054646522 |
| P(TH)BCR-ABL & PCR Plasma at 3 Mont,abs | 13 | -0.521978 | -2.029647 | 0.067291714 |
| P(Tyr)BCR-ABL & PCR Plasma at 3 Mont,abs | 13 | -0.483516 | -1.832033 | 0.094134688 |
| P(TH)BCR-ABL ratio & PCR at 3 Mont | 18 | -0.392121 | -1.705036 | 0.107523516 |
| P(TH)BCR-ABL ratio & PCR difference at 3 Mont | 18 | 0.392121 | 1.705036 | 0.107523516 |
| | | | | |
| BCR-ABL at 3 Month & PCR at 3 Month in Cells | 26 | 0.707867 | 4.909532 | 5.22884E-05 |
| BCR-ABL at 3 Month & PCR diff at 3 Month in Cells | 26 | -0.707867 | -4.909532 | 5.22884E-05 |
| BCR-ABL at 3 Month & PCR at 3 Month in Plasma | 21 | 0.839737 | 6.741019 | 1.92981E-06 |
| BCR-ABL at 3 Month & PCR at 3 Month in Plasma | 21 | 0.839737 | 6.741019 | 1.92981E-06 |
| p(TH)BCR-ABL & PCR at 3 Month Cells | 26 | 0.693062 | 4.709952 | 8.68196E-05 |
| p(TH)BCR-ABL & PCR diff at 3 Month Cells | 26 | -0.693062 | -4.709952 | 8.68196E-05 |
| p(TH)BCR-ABL & PCR at 3 Month plasma | 21 | 0.873248 | 7.811574 | 2.38349E-07 |
| p(TH)BCR-ABL & PCR at 3 Month plasm,abs | 21 | 0.301596 | 1.378829 | 0.183965445 |
| p(Tyr)BCR-ABL & PCR at 3 Month Cells | 26 | 0.709589 | 4.933551 | 4.91969E-05 |
| p(Tyr)BCR-ABL & PCR diff at 3 Month Cells | 26 | -0.709589 | -4.933551 | 4.91969E-05 |
| p(Tyr)BCR-ABL & PCR at 3 Month plasma | 21 | 0.814768 | 6.125516 | 6.88586E-06 |
| p(TH)BCR-ABL ratio & PCR at 3 Month Cells | 26 | 0.46996 | 2.608314 | 0.015411844 |
| p(TH)BCR-ABL ratio & PCR diff at 3 Month Cells | 26 | -0.46996 | -2.608314 | 0.015411844 |
| p(TH)BCR-ABL ratio & PCR at 3 Month plasma | 21 | 0.536827 | 2.773494 | 0.012101821 |
| p(TH)BCR-ABL ratio & PCR at 3 Month plasma, abs | 21 | 0.644587 | 3.675049 | 0.001608669 |
| p(Tyr)BCR-ABL ratio & PCR at 3 Month Cells | 26 | 0.383198 | 2.032425 | 0.053318262 |
| p(Tyr)BCR-ABL ratio & PCR at 3 Month Cells | 26 | -0.383198 | -2.032425 | 0.053318262 |
| p(Tyr)BCR-ABL ratio & PCR at 3 Month plasma | 21 | 0.35679 | 1.664778 | 0.112361453 |
| p(Tyr)BCR-ABL ratio & PCR at 3 Month plasma,abs | 21 | 0.757603 | 5.059349 | 6.96437E-05 |

FIG. 11

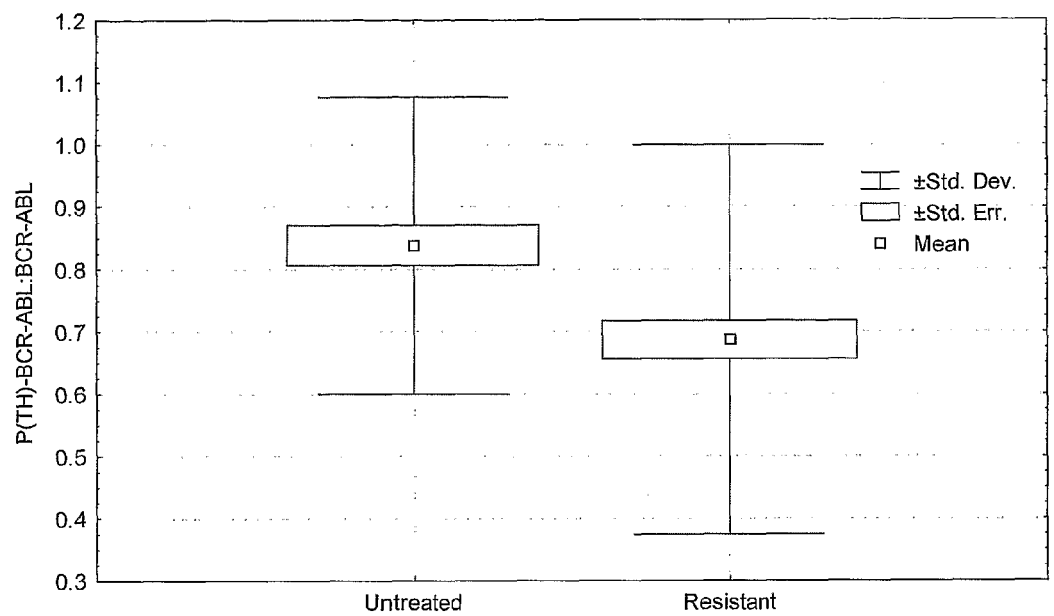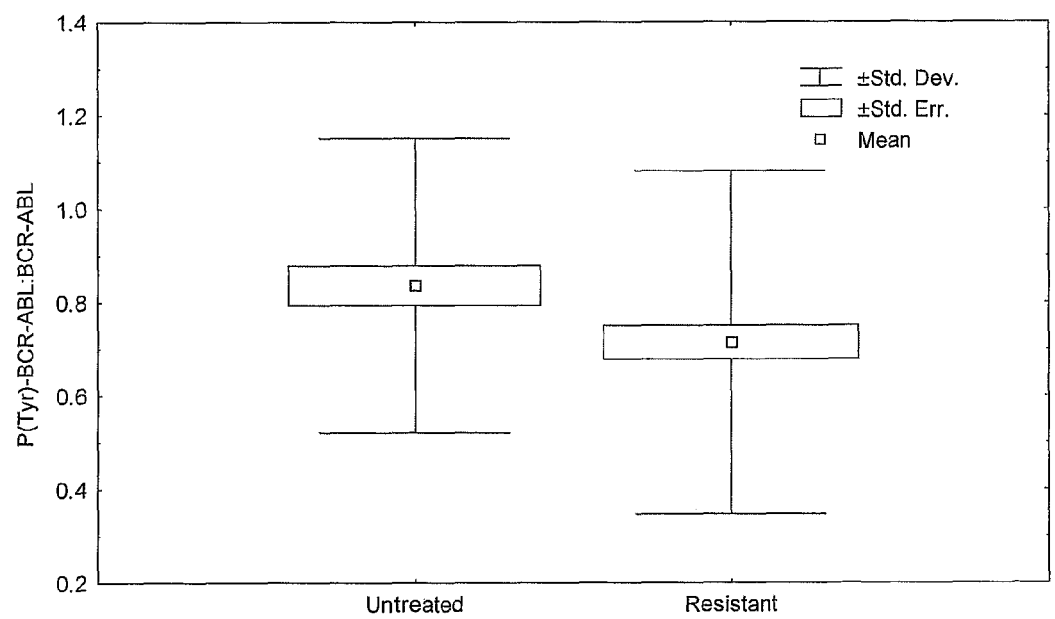
FIG. 13

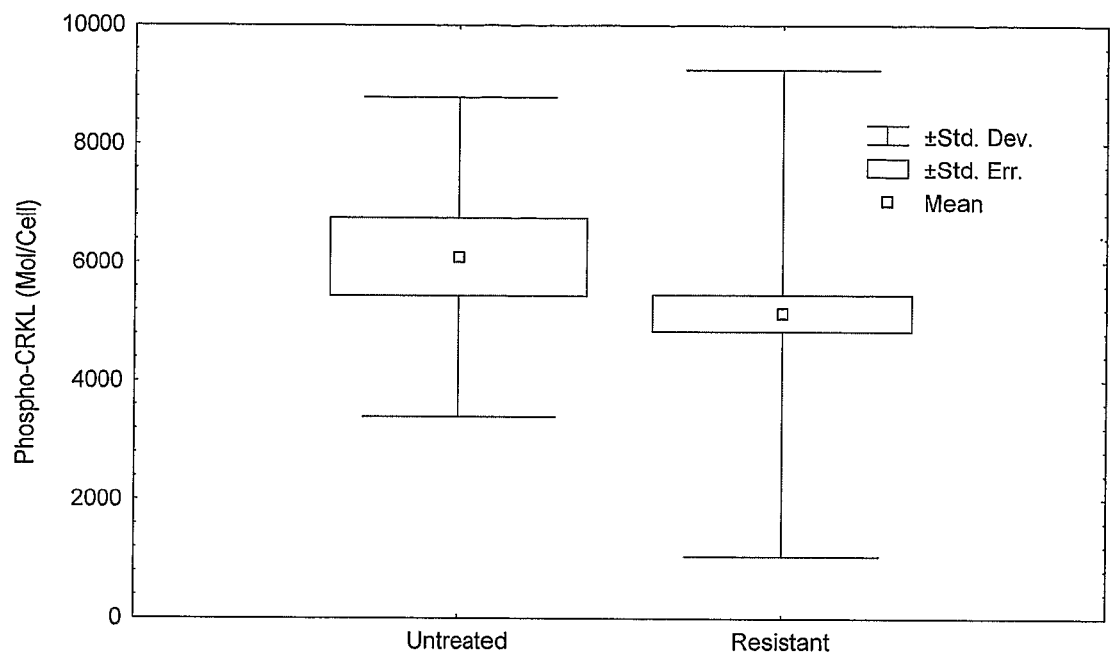
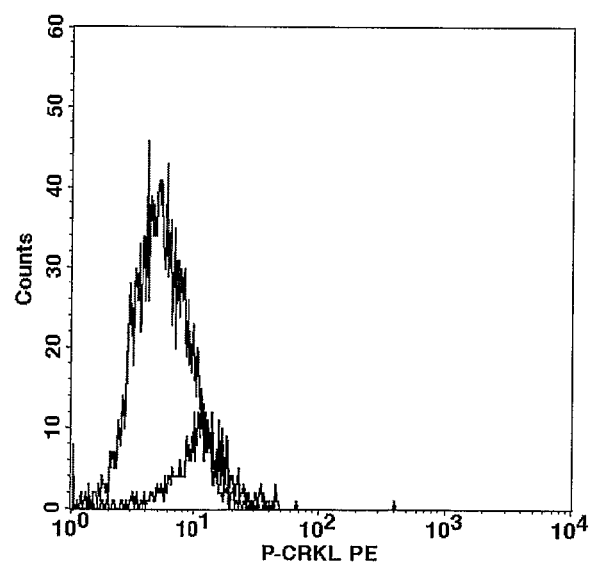
FIG. 14

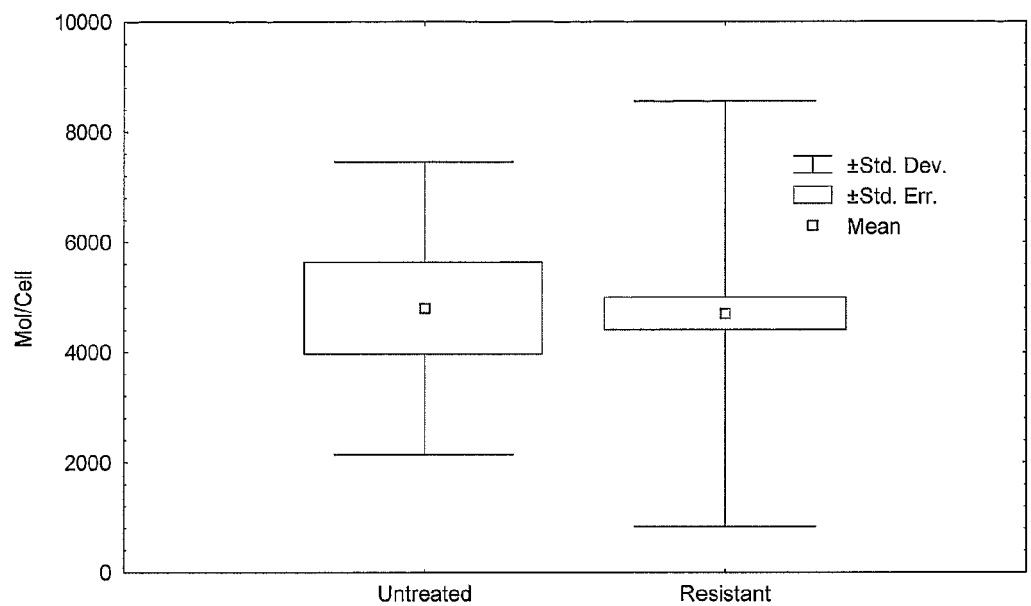
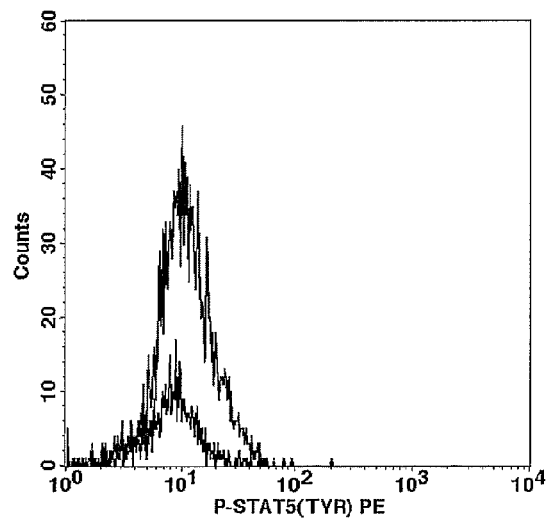
FIG. 16

QUANTIFICATION OF FUSION PROTEINS AND THEIR ACTIVITY FROM CHROMOSOMAL TRANSLOCATION

This application claims priority to U.S. Provisional Patent Application Ser. No. 60/738,141, filed Nov. 18, 2005, which is incorporated by reference herein in its entirety.

FIELD OF THE INVENTION

The present invention concerns at least the fields of molecular biology, cell biology, and medicine. In particular, the field of the present invention includes cancer therapy.

BACKGROUND OF THE INVENTION

Chromosomal translocations bring two previously unlinked regions of the genome together and in certain cases can result in disease by inducing synthesis of a novel fusion protein. This phenomenon is significant when the breakpoint of the translocation affects an oncogene, for example, and results in cancer.

The exemplary BCR/ABL fusion protein is a constitutively-active tyrosine kinase present in patients with chronic myeloid leukemia (CML) as well as some patients with acute lymphoblastic leukemia (ALL) with the Philadelphia chromosome (9:22) translocation. Recently, this fusion tyrosine kinase protein has been successfully targeted for therapy through the use of specific tyrosine kinase inhibitors such as STI571 (Gleevec). Despite the success of such a drug, a significant number of patients (10-30%) have demonstrated poor response, as well as development of resistance to therapy. Therefore, it is increasingly important to be able to monitor the activity of the BCR/ABL protein in response to therapy as a means to monitor efficacy and response, as well as a potential diagnostic tool, or as well as predicting response or prognosis. Discovery of resistance to therapy by Gleevec due to mutational abnormalities within the BCR/ABL gene, or other exemplary mechanisms, has led to the emergence of new drugs such as BMS-354825 and AMN107 to target these resistant forms of the BCR/ABL protein. Therefore, there is significant need to develop means of monitoring effects of Gleevec therapy at early stages. Direct evaluation of BCR/ABL protein activity (phosphorylation) or levels has been limited due to the large size of the protein (190 or 210 kD). Evaluation usually has been largely based on western blot or immunoprecipitation techniques, both of which are difficult to implement in clinical laboratories for patient samples. As a result, downstream modulators such as AKT and CRK-L proteins have been used to monitor BCR/ABL activity. Although monitoring of such downstream signaling molecules has proved effective, mainly through western blot analysis, a direct and quantitative measure of the levels and activation of the BCR/ABL protein itself is desired.

The LightCycler quantification kits (Roche Molecular Biochemicals) reverse transcribe cDNA from RNA and a partial fragment of the mRNA is amplified using specific primers. Following this, the amplicon is detected using specific hybridization probes.

Talpaz et al. (2000) describe autoantibodies to Abl and Bcr proteins in Philadelphia (Ph) chromosome-positive leukemias.

Valk et al. (2003) describe qualitative RT-PCR assays and real-time quantitative RT-PCR assays using commercially available sequence detection systems, particularly for detecting increased sensitivity minimal residual disease studies.

van Denderen et al. (1990) regards polyclonal antiserum raised against a synthetic peptide corresponding to the bcr-abl junction in $P190^{bcr-abl}$, and immunoprecipitation utilizing antibodies directed thereto identified specificity against $P190^{bcr-abl}$ but not $P210^{bcr-abl}$.

Wallace et al. (2003) describe two-stage multiplexing comprising polymerase chain reaction with multiplex detection on spectrally addressable liquid bead microarrays, such as for identifying seven exemplary fusion transcripts in lymphoblastic leukemia.

U.S. Pat. No. 5,369,008 relates to detecting BCR-ABL in a sample by assaying for binding of an antibody to BCR-ABL, particularly upon binding of the antibody to the SH2 region of the ABL gene product.

WO 95/15331 concerns detection of specific fusion proteins, such as by contacting a sample with two antibodies, each of which are capable of binding to a different region of the fusion protein.

U.S. Pat. No. 6,686,165 regards detecting chromosomal aberrations by binding separately-targeted probes for a tumor-specific protein and detecting them by flow cytometry. In specific embodiments, the chromosomal aberrations are employed as targets for monitoring the level of residual disease during and after therapy.

A specific, and in certain aspects, quantitative measure of the levels and activation of a fusion protein itself is desired and provided by the novel disclosure of the present invention. The present invention also employs novel methods for monitoring therapy for a disease.

SUMMARY OF THE INVENTION

The present invention generally concerns detection of fusion proteins and their activity, in which the fusion proteins were generated as a result of chromosomal translocation in one or more cells, and in particular aspects the fusion proteins are representative of a disease in an individual, such as cancer, for example. In certain aspects, the fusion proteins or their activity (their activation reflected by a phosphorylated state, in exemplary embodiments) are utilized as an indicator for prognosis of the disease and/or responsiveness of a therapy thereto. Thus, there are provided methods of monitoring a therapy, predicting a response to therapy, determining a diagnosis, and/or detecting minimal residual disease and/or prognosis of disease of an individual, for example. In specific embodiments of the invention, it regards monitoring a therapy in an individual having one or more cells comprising the fusion protein. In monitoring treatment or progression of a disease, samples may be obtained from an individual at different timepoints, such as before, during, and/or after a therapy for a disease, such as cancer. In particular embodiments, the amount of a probe/fusion protein complex or levels of their activity (reflected by their phosphorylated state, for example) from a sample of an individual and/or the amount of one or more characteristics of fusion proteins from a sample of the individual are compared to their respective counterparts obtained at a different timepoint. A difference in the amount of the probe/fusion protein complex and/or the amount of one or more characteristics (such as activation, including by phosphorylation, for example) of fusion proteins is correlated to success of the therapy and/or progression of the disease, for example.

In certain embodiments, there is a method of monitoring a therapy for an individual that targets a fusion protein from a chromosomal translocation, comprising a first assaying of one or more characteristics of a fusion protein from a sample of the individual; subjecting the individual to the therapy; and a second assaying of a sample from the individual for one or more characteristics of a fusion protein from a sample of the individual. In alternative embodiments, however, the therapy is a cancer therapy (for example, a generally cytotoxic drug) yet it does not target a fusion protein from a chromosomal translocation. Assaying methods may comprise subjecting the sample to a first probe that is capable of binding a first region of the fusion protein, wherein binding of the first probe to the first region produces a first probe/fusion protein complex; subjecting the first probe/fusion protein complex to a second probe that is capable of binding a second region of the fusion protein, wherein binding of the second probe to the second region produces a second probe/fusion protein complex; and detecting the second probe/fusion protein complex.

In some embodiments of the invention, the methods involve monitoring of a therapy for an individual, and in certain aspects the therapy targets one or more characteristics of a fusion protein produced by chromosomal translocation in at least one cell of the individual. In specific aspects, the therapy comprises a kinase inhibitor, an antibody, or a cytotoxic drug, for example. In certain aspects, the one or more characteristics refers to one or more traits of the protein that are capable of being monitored, such as a post-translational modification or a mutation, for example. In further aspects, the one or more characteristics being targeted comprises phosphorylation; glycosylation; acetylation; a mutation, such as a deletion, insertion, reversion, or point mutation, for example; or a combination thereof.

In some aspects, assaying of one or more characteristics is further defined as quantitating one or more characteristics of the fusion protein, for example quantitating phosphorylation of one or more fusion proteins in the sample. A first or second probe may recognize a mutation in the fusion protein, such as one that confers resistance to a cancer therapy for the individual, for example. In specific embodiments, there is correlation between the level of the fusion protein and the level of the fusion mRNA from a sample.

In specific embodiments of the invention, following assaying of the fusion protein, the individual is subjected to an alternative therapy. The alternative therapy may be employed upon determination of the therapy being considered unsuccessful, such as based upon determination of the one or more characteristics following the cancer therapy. An alternative therapy may continue to comprise the original therapy and include an additional therapy, or the alternative therapy may not employ the original therapy at all.

The monitoring of the fusion protein may be further defined as determining resistance to a cancer therapy of the individual, such as determining resistance to a kinase inhibitor, an antibody, or a cytotoxic drug, for example. In specific aspects, resistance to Gleevec is developed. When the individual has resistance to a cancer therapy, an alternative cancer therapy may be administered to the individual.

In specific aspects of the invention, the detection of the fusion protein utilizes a substrate, such as beads, for example. The probe may be linked to the substrate covalently or noncovalently. In particular aspects, the substrate comprises a first probe that is capable of binding the fusion protein, such as by utilizing antibodies as the first probe against a first region of the fusion protein for immunoprecipitating the fusion protein. Then a second probe that is capable of binding a second region of the fusion protein, such as another antibody, is used for detecting the fusion protein or is otherwise structured to be detectable in the fusion protein/substrate complex. When the second probe is labeled, such as with a fluorochrome, for example, the fused protein can be detected and quantified.

The present invention concerns the identification of chromosomal translocations from a sample in an individual, wherein the chromosomal translocations are identified by assaying for fusion proteins generated therefrom. Assaying for the fusion proteins comprises utilizing a substrate (such as beads, for example) and antibodies for each of the separate regions of the fusion proteins. In a particular aspect, a first antibody for a first region of a fusion protein is affixed to a bead, and a sample comprising a fusion protein generated from chromosomal translocation is subjected to the first antibody-affixed bead. When the fusion protein is recognized and binds the first antibody-affixed bead, there is produced a fusion protein-bead complex. The fusion protein-bead complex is subjected to a second antibody that recognizes a second region of the fusion protein, wherein the second region is nonidentical to the first region. Identification of at least one detectable moiety on the second antibody identifies the binding of the second antibody to the second region of the fusion protein bound by the first antibody on the fusion protein-bead complex. In specific embodiments, the detection identifies that a chromosomal translocation occurred. In further embodiments, the identification of chromosomal translocation and/or the identification of one or more fusion proteins in the sample indicates that the individual has at least one cancerous cell or is at risk for developing cancer, said cancer characterized by the presence of a fusion protein.

In specific aspects of the invention, the fusion protein generated by the chromosomal translocation is comprised of at least two parts as a result of the translocation event: a first part of the fusion protein is encoded by at least part of one protein-encoding polynucleotide (which may be referred to as a gene) on a chromosome, whereas a second part of the fusion protein is encoded by at least part of another protein-encoding polynucleotide (which may also be referred to as a gene) on a chromosome. In the invention, the first and second antibodies recognize different parts of the fusion protein.

Particular embodiments of the invention include monitoring phosphorylation before and after a therapy, for example before and after administration of one or more cancer therapies at least one of which comprises a kinase inhibitor. In specific embodiments, the level of phosphorylation is monitored. The amount of phosphorylation in a representative number of fusion proteins may be determined before and after a therapy that targets phosphorylation. In specific aspects, levels of phosphorylation before therapy predicts a response to therapy. In certain aspects, an individual is identified as having a higher chance of being resistant to a therapy, and in specific embodiments of the invention an alternative therapy is employed, such as by using combination therapy rather than a single agent, for example. Furthermore, after initiating therapy, the identification of levels of phosphorylation is beneficial. The present inventors have demonstrated that in some individuals there is selection of cells that have higher phosphorylation after initiating therapy. In this particular case, the average cells (such as cells having fusion proteins with average phosphorylation quantities) that initially were dominant (wherein the overall phosphorylation before therapy is not increased) die out with therapy, and the cells having fusion proteins with high phosphorylation remain intact and become dominant. Therefore, monitoring phosphorylation while on therapy can be beneficial to the individual, such as by predicting response to therapy that targets phosphorylation, including kinase inhibitors.

For use in the methods of the present invention, a sample can be obtained from various physiological sources in an individual, such as a patient, including whole blood, bone marrow, plasma, cerebrospinal fluid, semen, urine, nipple aspirate, or a solid tumor from the spinal cord, for example. Solid tumors can be disrupted by any means known in the art such as by homogenization, for example, prior to analysis.

Antibodies employed in the invention may comprise markers such as, for example, radioisotopes, enzymes, fluorogens, chromogens, and chemiluminescent labels. Suitable radioactive labels include tritium, carbon 14, phosphorous 32, iodine 125 or 131, yttrium-90, technetium-99m or sulfur 35. Examples of various suitable radioactive labels are described in U.S. Pat. No. 4,062,733, incorporated herein by reference. Examples of various enzymatic markers include alkaline phosphatase, horseradish peroxidase, luciferase, β-galactosidase, glucose oxidase, lysozyme, malate dehydrogenase and the like. Suitable substrates for the enzymatic systems include simple chromogens and fluorogens such as, for example, paranitrophenyl, phosphate, β-D-glucose, homovanillic acid, o-dianisidine, bromocresol purple, 4-methyl-umbelliferone and indoxyl phosphate. Chromogenic labels are compounds that absorb light in the visible ultraviolet wavelengths. Such compounds are usually dyes. Fluorogenic compounds emit light in the ultraviolet or visible wavelengths subsequent to irradiation by light or other energy source. A representative listing of suitable fluorogens are described in U.S. Pat. Nos. 4,366,241 and 3,996,345, both of which are incorporated herein by reference. Chemiluminescent labels include, for example, those identified in U.S. Pat. No. 4,104,029, which is incorporated herein by reference. Depending on the nature of the label or signal-generating system used, a signal can be detected by any appropriate means known in the art. For example, in the case of a radioactive label, X-ray film can be used to develop the signal. For fluorescent labels, a signal can be detected by irradiating with light and observing the level of fluorescence in a fluorometer. For enzyme-catalyzed systems, a color change can be detected visually for a positive reaction when a chromogenic label is used. Further quantification of an enzymatic reaction can be accomplished with a densitometric analysis.

In certain aspects of the invention, the first probe, the second probe, or both are labeled. The labels may comprise a chromagen, radioactivity, a fluorophore, quantum beads, and so forth. In particular aspects, the ratio of second probe molecule to label is a 1:1 ratio (one molecule:one chromogen), allowing specific and reproducible quantification of the detectable molecule. By comparing the number of detected chromogens, the number of detected fusion molecules can be quantified in the sample (for example, in 10 cc of plasma or serum or in 100 cells).

In certain aspects, the present invention is useful for detecting translocations that are difficult to detect by conventional cytogenetics, complex translocations that involve several chromosomes, cytogenetically silent translocations, and/or situations wherein karyotype studies failed or were not conclusive.

In particular embodiments, the present invention concerns free circulating BCR-ABL protein and its phosphorylation in monitoring patients with chronic myeloid leukemia.

In specific embodiments, there is a method of monitoring a therapy for an individual who has received at least one course of therapy, wherein said therapy targets a fusion protein from a chromosomal translocation, said protein comprised of a first region and a second region, comprising assaying one or more characteristics of the fusion protein from a sample of the individual, said assaying comprising: subjecting the sample to a first probe that is capable of binding said first region of the fusion protein, wherein binding of the first probe to the first region produces a first probe/fusion protein complex; subjecting the first probe/fusion protein complex to a second probe that is capable of binding said second region of the fusion protein, wherein binding of the second probe to the second region produces a second probe/fusion protein complex; and detecting the second probe/fusion protein complex, wherein said detecting results in the assaying of said one or more characteristics.

Methods of the invention may further comprise assaying one or more characteristics of the fusion protein from a sample of the individual prior to the individual receiving the therapy. In particular embodiments, the assaying prior to the therapy comprises subjecting the sample to a first probe that is capable of binding a first region of the fusion protein, wherein binding of the first probe to the first region produces a first probe/fusion protein complex; subjecting the first probe/fusion protein complex to a second probe that is capable of binding a second region of the fusion protein, wherein binding of the second probe to the second region produces a second probe/fusion protein complex; and detecting the second probe/fusion protein complex.

In a specific embodiment, the fusion protein is further defined as an activated fusion protein. In particular aspects, the therapy targets one or more characteristics of the fusion protein. In specific embodiments, the therapy comprises a kinase inhibitor, an antibody, or a cytotoxic drug. In particular aspects, one or more characteristics comprises phosphorylation, glycosylation, acetylation, a mutation, or a combination thereof. The mutation may be a deletion, inversion, or point mutation. In specific embodiments, the first probe is linked to a substrate, such as one that comprises a bead, plate, or a column; the substrate may also be immobilized. In a specific embodiment, the fusion protein is Bcr-Abl.

In additional embodiments, when the substrate comprises a bead, the number of fusion molecules may be quantified. In specific embodiments, the quantification utilizes the following formula: percentage of beads that comprise one or more molecules×median number of molecules on the beads that are positive=number of molecules in the sample. A particular therapeutic regimen may be employed upon said quantifying.

A sample of the invention may be further defined as comprising cell lysate, plasma, blood, serum, or mixture thereof. In particular aspects, the sample is from cerebrospinal fluid, blood, urine, serum, plasma, nipple aspirate, feces, cheek scrapings, saliva, biopsy, ascites, or a mixture thereof.

In another embodiment of the invention, the first assaying, second assaying, or both of one or more characteristics is further defined as quantitating a characteristic of the fusion protein, such as quantitating phosphorylation of one or more fusion proteins in the sample. The second probe may be further defined as being capable of detecting activation of the fusion protein. In particular aspects, the first probe, second probe, or both comprise anti-phosphotyrosine activity or anti-phospho-serine activity. In specific embodiments, the second probe comprises a label, such as a chromagen, radioactivity, a fluorophore, or a combination thereof, for example. For quantification, the ratio of a molecule of the second probe to the label may be about a 1:1 ratio. Also, methods of the invention may further comprise determining the number of fusion molecules in the sample based on the number of labeled second probes. In a specific aspect, the first probe, second probe, or both recognizes a mutation in the fusion protein, such as one that confers resistance to a cancer therapy for the individual, for example. In particular aspects, detection of the second probe-fusion protein complex identifies the individual as requiring an alternative therapy.

The individual may have cancer, may be suspected of having cancer, or may be at risk for developing cancer. The cancer may be leukemia, lymphoma, brain cancer, lung cancer, breast cancer, colon cancer, prostate cancer, liver cancer, head and neck cancer, skin cancer, ovarian cancer, cervical cancer, pancreatic cancer, stomach cancer, spleen cancer, thyroid cancer, testicular cancer, or bone cancer.

In some embodiments of the invention, following the second assaying the individual is subjected to an alternative therapy. In other aspects of the invention, monitoring is further defined as determining resistance to a cancer therapy of the individual. The resistance may be developed to a kinase inhibitor, an antibody, or a cytotoxic drug. The resistance may be developed to Gleevec. In a specific embodiment, when the individual has resistance to a cancer therapy, an alternative cancer therapy is administered to the individual.

In specific embodiments of the invention, therapy affects the phosphorylation status of a fusion protein from a chromosomal translocation, wherein the first region comprises a phosphorylation site, and wherein the assaying is further defined as assaying the phosphorylation status of the fusion protein.

In particular embodiments, the method is further defined as quantifying the tumor bulk in the individual.

In specific aspects of the invention, resistance to a cancer therapy is due at least in part to inability of the therapy, such as imatinib, for example, to bind and suppress the fusion protein, for example BCR-ABL, due to point mutations, alterations in phosphorylation state or other postranslational processing, or in cases where no mutations are present, to the activation of other pathways that render the disease resistant, for example.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 11 provides a table showing correlations between levels of BCR-Abl and its phosphorylation with various laboratory and clinical findings.

FIGS. 13A-13B show BCR-ABL phosphorylation from imatinib-naive and imatinib-resistant CML patients. Ratios of p-BCR-ABL to total BCR-ABL protein show that cells from imatinib-resistant CML patients had significantly lower levels of (FIG. 13A) p-BCR-ABL (Thr) and (FIG. 13B) p-BCR-ABL (Tyr245) than cells from imatinib-naive patients.

FIGS. 14A-14B show CrkL phosphorylation in cells from imatinib-naive and imatinib-resistant CML patients. In FIG. 14A, quantitation of intensities of p-CrkL (molecules/cell) show that imatinib-resistant CML patients had significantly lower levels of p-CrkL per cell than imatinib-naive patients. In FIG. 14B, representative flow cytometry histogram of phosphorylated CrkL intensities in blast cells illustrates decreased p-CrkL intensity but increased event count (blast cells) in a resistant (purple) versus naive (black) sample.

In FIG. 15A, quantitation of p-Akt intensities (molecules/cell) shows that cells from imatinib-resistant patients had significantly lower levels of p-Akt than cells from imatinib-naive patients. In FIG. 15B, representative flow cytometry histogram of phosphorylated Akt intensities in blast cells illustrate decreased p-Akt intensity but increased event count (blast cells) in a resistant (purple) versus naive (black) sample.

FIGS. 16A-16B show STAT5 phosphorylation in CML cells from naive and imatinib-resistant patients. In FIG. 16A, quantitation of p-Stat5 intensities showed no significant difference in the mean number of molecules per CML cell between imatinib-resistant and -naive patients. In FIG. 16B, representative flow cytometry histogram of phosphorylated STAT5 intensities in blast cells illustrates comparable p-STAT5 intensity but increased event count (blast cells) in a resistant (purple) versus naive (black) sample.

DETAILED DESCRIPTION OF THE INVENTION

I. Definitions

Figure 1:
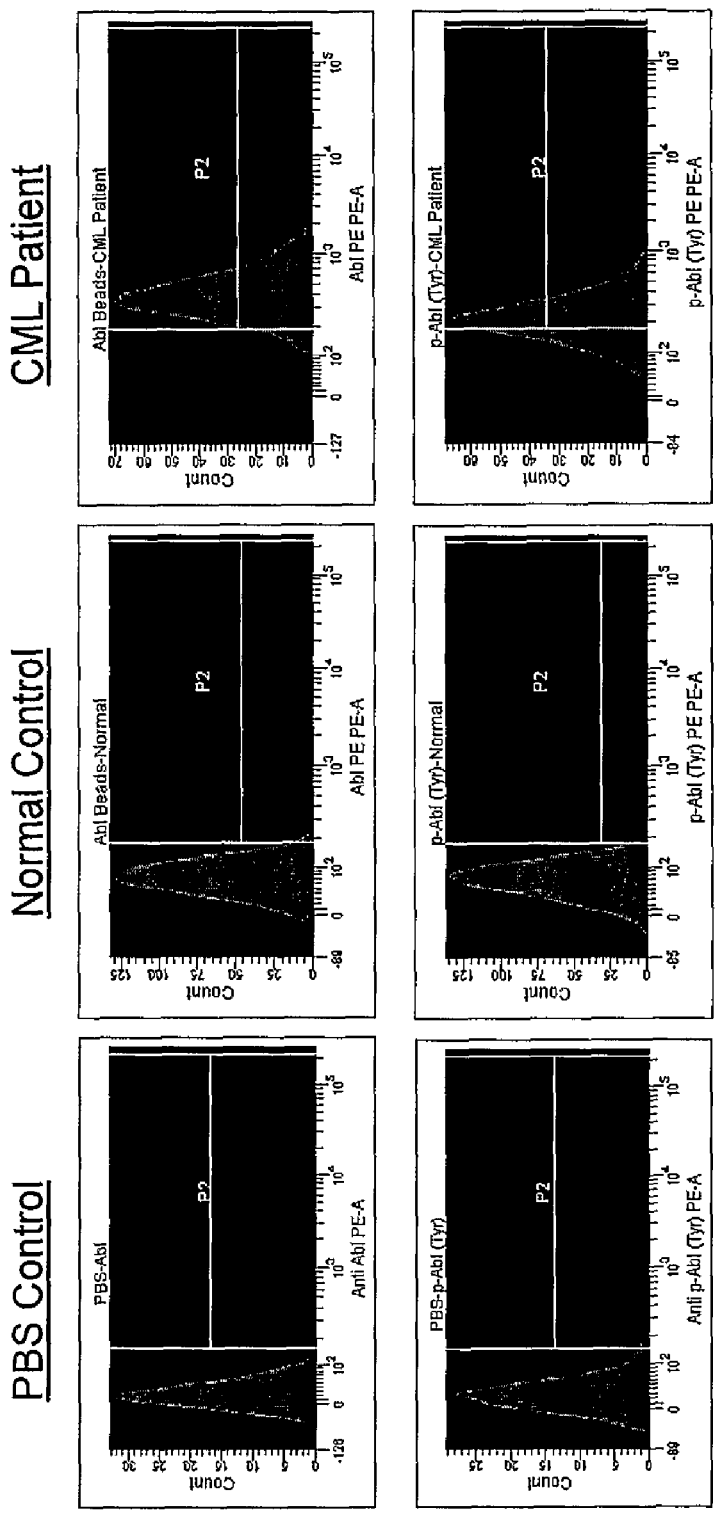
FIG. 1 shows detection of BCR-ABL protein and its phosphorylation using bead and flow cytometry. Plasma samples prepared from peripheral blood of normal subjects and CML patients were incubated with anti-BCR coated beads, followed by incubation with antibody directed against ABL (upper row) or phosphorylated Tyr-245 of ABL (lower row). PBS served as a negative control. A lysate of the CML-derived cell line, K-562, served as a positive control (not shown).

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "activation" as used herein refers to changes in the protein that enhance its function. This is usually accomplished by phosphorylating specific segments of the protein, but other changes, such as fenestration, acetylation, and others, for example, known in the art can also play a role in the activation of the protein. The current invention is designed to specifically detect these modifications.

The term "at risk for developing cancer" as used herein refers to an individual that has one or more risk factors for developing cancer, and in specific embodiments the invention is employed for such. Examples of risk factors include family history of cancer, advanced age, benign tumors, cells with abnormal DNA, environmental factors, such as use of tobacco products, exposure to sun, and carcinogens, for example, gender, previous abnormal biopsy, race, diet, lifestyle choices, exposure to radiation or other cancer-causing agents, certain genetic changes, and/or nutrition. In particular, risk factors for developing leukemia, for example, include exposure to high levels of radiation, including from the environment or medical treatment; exposure to certain chemicals, such as benzene or formaldehyde, for example; chemotherapy, such as with alkylating agents, for example; Down syndrome and certain other genetic diseases; exposure to human T-cell leukemia virus-I (HTLV-I), which causes a rare type of chronic lymphocytic leukemia known as human T-cell leukemia; and Myelodysplastic syndrome, which is a blood disease, and afflicted individuals are at increased risk of developing acute myeloid leukemia, for example.

The term "chromosomal translocation" as used herein refers to an event wherein a fragment of one chromosome is broken off and is then attached to another chromosome, which may be of a different pair, in specific embodiments. In specific aspects of translocations of the invention, the molecules are tumor-specific because the chimeric RNA and subsequent protein product only reside in the cell with the chromosomal translocation, which is beneficial for diagnostic and therapeutic applications. In alternative embodiments, translocations that result in enforced proto-oncogene expression do not provide cell-specific diagnostic because the proto-oncogene is also expressed in normal cells. The translocations are generally between non-homologous chromosomes but can be between homologous chromosomes. In particular, the fusion gene products generated by the chromosomal translocation are intracellularly located. Polynucleotides (which may be referred to herein as genes) that may be affected by chromosomal translations include gene fusions wherein the breakpoints reside within introns of the affected genes on the two chromosomes of concern, for example.

The term "fusion protein" as used herein refers to a polypeptide encoded by a polynucleotide wherein the polynucleotide is the result of fusion between at least two polynucleotides, such as from two different genes, including the polynucleotides that result upon chromosomal translocation. In other words, the fusion protein comprises at least two different regions: one region encoded from one polynucleotide or gene and a second region encoded from another polynucleotide or gene.

The term "resistance" or "resistant therapy" as used herein refers to a medical condition in an individual that is not responsive to a therapy. In specific embodiments, the terms refer to cancer that is resistant to a cancer therapy or becomes resistant to a cancer therapy. In specific embodiments, the terms may be further defined as concerning a cancer wherein cancer cells are not killed by the therapy or even may proliferate during the therapy treatment or shortly thereafter, such as within months, weeks, or days. The resistance may be de novo resistance or acquired resistance.

The term "sample" as used herein refers to a representative entity from any organism, including humans, animals, and plants, as well as cell cultures, recombinant cells, cell components, and environmental sources, for example. They may comprise a biological tissue, fluid, or specimen. Samples may be obtained from any animal, including, a mammal, for example, human, horse, dog, cat, sheep, goat, cow, and pig. Samples may include, but are not limited to, amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, urine, and the like. Samples may also be processed, such as sectioning of tissues, fractionation, purification, or cellular organelle separation.

The term "tumor load" as used herein refers to the amount of cancer cells, the tumor size, or the amount of cancer in an individual. In specific embodiments, the tumor load may be referred to as "tumor burden."

The practice of the present invention may employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS 1N MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

II. The Present Invention

The present invention generally concerns the detection of fusion proteins and/or their activation, including those resulting from a chromosomal translocation. In particular, response to a therapy is monitored using methods of the invention, and in other aspects a disease such as cancer is predicted, diagnosed, and/or prognosticated. In certain aspects, the methods and compositions of the invention are employed to monitor fusion protein activity and/or level. In specific embodiments, the present invention is utilized to do one or more of the following: 1) diagnose a medical condition, including providing information regarding the stage of a medical condition; 2) predict response or prognosis of an individual having disease or suspected of having disease; and 3) monitor efficacy and response of a therapy.

In certain embodiments, a first probe that recognizes a first region of the fusion protein is immobilized to a substrate and a sample comprising the fusion protein or suspected of comprising the fusion protein is subjected to the substrate under conditions wherein the first probe binds at least part of the first region of the fusion protein. The first probe-fusion protein-immobilized complex is then subjected to a second probe for recognition of the fusion protein under conditions to detect the second probe or the binding of the second probe to the immobilized complex.

In specific embodiments, the present invention is used for detection of an exemplary fusion protein associated with cancer, such as leukemia. The present inventors developed simplified methods for measuring the levels of the exemplary fusion protein BCR/ABL and its phosphorylation, and these methods can be used in routine clinical laboratories or even for follow-up tests in patients. The assay can effectively be used for cell lysate samples, but since the present inventors have demonstrated previously that leukemic cells release their proteins into circulation, such as cCD20 and cCD52, the present inventors tested plasma from patients with CML for levels of BCR/ABL and its phosphorylation. This is based upon the specific embodiment that due to turnover and breakdown of cells, protein complexes circulate freely in plasma or serum. Here, the present inventors demonstrate that the plasma from patients with CML provides an excellent source for testing levels of BCR/ABL protein as well as its phosphorylation, with sensitivity comparable to that of PCR-based assyas for measuring minimal residual disease. More importantly, the exemplary BCR/ABL protein assay provides valuable information on the kinase activity of the BCR/ABL protein.

III. Exemplary Chromosomal Translocation-Generated Fusion Proteins

Chromosomal translocations occur in many different cancers, and the present invention is applicable to identification of any fusion protein, including any chromosomal translocation-generated fusion protein. In specific embodiments, the cancer includes leukemias, lymphomas, sarcomas, and some epithelial tumors, for example. A breakdown in the normal process of immunoglobulin or T-cell-receptor gene rearrangement can cause chromosomal translocations in leukemias and lymphomas, for example, which results in interchromosomal translocations rather than normal intrachromosomal rearrangement. The present invention concerns fusion proteins generated from any chromosomal translocation, and in particular aspects these fusion proteins may provide tumor-specific diagnosis, prognosis, monitoring of therapy, and/or tumor-specific targets for therapies customized to a cancer cell.

In particular, hematopoietic cancer blast cells from individuals with acute myeloid and lymphoid leukemias often comprise certain chromosomal translocations, which may result from fusion proteins that affect normal hematopoietic homeostasis, for example. Some chromosomal breakpoints result in acute myeloid leukemia (AML), acute lymphoid leukemia (ALL), and chronic myeloid leukemia (CML).

In an exemplary embodiment, there is the Bcr-Abl fusion protein, such as the Philadelphia (Ph')-positive ALL being highly associated with two forms of chimeric bcr-abl proteins: $P190^{bcr-abl}$ and $P210^{bcr-abl}$. In specific embodiments, AML may result from t(8; 21) and the fusion AML1/ETO; t(15; 17) and the fusion protein PML/RARa; and inv(16) and the fusion protein CBFb/MYH11, which respectively result in the following particular types of AML: AML-M2; APL; and AML-M4Eo. In additional specific embodiments, ALL results from t(9; 22) and the fusion protein BCR-ABL and t(4; 11) and the fusion protein MLL/AF4. CML may result from t(9; 22). TEL/AML1 fusions are associated with leukemia and are difficult to see by conventional cytogenetics, including the exemplary t(12; 21)(p13; q22). The t(8; 14) fusion protein involving the c-myc gene may also be addressed with the invention.

Another well-studied example of a translocation generating cancer is seen in Burkitt's lymphoma. In most cases of this B cell tumor, a translocation is seen involving chromosome 8 and one of three other chromosomes (2, 14 or 22). In these cases, a fusion protein is not produced, but rather, the c-myc proto-oncogene on chromosome 8 is brought under transcriptional control of an immunoglobulin gene promoter. In B cells, immunoglobulin promoters are transcriptionally quite active, resulting in overexpression of c-myc, which is known from several other systems to have oncogenic properties. Hence, this translocation results in abberent high expression of an oncogenic protein, which almost certainly is at the root of the Burkitt's tumor.

Other examples of translocation breakpoints associated with human cancer include: 14:18 translocation in follicular B cell lymphomas (bcl-2 and immunoglobulin genes); 15:17 translocation in acute promyelocytic leukemia (pml and retinoic acid receptor genes); and 1:19 translocation in acute pre-B cell leukemia (PBX-1 and E2A genes)

Certain fusions may be found exclusively or highly preferentially in specific cell types, such as FUS-CHOP in adipocytes of liposarcoma and MLL-MLLT3 in myeloid cells of acute myeloid leukemia, for example. PML/RAR-alpha protein, which results from the t(15; 17) translocation, may be detected with the invention.

The $M4E_o$ subtype of acute myeloid leukemia (AML) can be caused by a chromosomal aberration comprising a pericentric inversion of chromosome 16, inv(16), which results in the fusion of the core-binding factor β subunit (CBFB) gene (also known as PEBP2B) at chromosome band 16q22 and the myosin heavy polypeptide 1 (MYH1) gene at chromosome band 16p13 (the fusion protein thereof may be referred to as CBFB-MYH1). In the M2 subtype of AML, there can be the t(8; 21) translocation that results in the fusion of AML1 gene at chromosome band 21q22 and the myeloid translocation gene on chromosome 8 (MTG8) at chromosome 8q22, producing the AML1-MTG8 fusion protein.

Leukemic cells of patients with therapy-related myelodysplastic syndromes and therapy-related acute myelogenous leukemia (t-MDS/AML) include chimeric fusions from t(7; 11) and t(2; 11) of FXFG repeats of NUP98 with the homeodomains of HOXA9 and HOXD13, respectively; the inv(11) (p15q22) fuses the NUP98 FXFG repeats with DDX10 (Nakamura et al., 1996; Borrow et al., 1996; Raza-Egilmez et al., 1998; Yasuhito et al., 1997). The t(11; 20)(p15; q11) chromosomal translocation results in NUP98-TOP1 fusion (Ahuja et al., 1999).

Translocations in solid tumors, such as t(2; 7); t(4; 9); t(1; 13); t(9; 17), may also be detected.

IV. Preparation of Substrate-Probe Complex

In specific aspects, the present invention employs a probe to part of a chromosomal translocation-derived fusion protein, wherein the probe is affixed to a substrate. In specific embodiments, the substrate may be of any kind so long as it is suitable for affixation of antibodies and so long as it is suitable for being subjected to a sample comprising a chromosomal translocation-derived fusion protein or suspected of comprising a chromosomal translocation-derived fusion protein. In further specific embodiments, the substrate is a bead, which itself may be immobilized, or it may be a microarray, microtiter plate, or microtiter slide, for example.

The attachment of the probes to the substrate may be achieved by any suitable method so long as the probes are suitable placed to allow recognition of chromosomal translocation-derived fusion protein. There are a variety of methods to attach probes to a substrate, although in particular aspects the attachment is chemical, such as a covalent attachment between the antibody and the substrate, although non-covalent attachments may be employed. In further specific embodiments, the attachment of the antibody to the substrate is via a protein bond. Other means for attachment, such as double affinity antibodies or peptide binding, for example, may also be used.

Probes may be of any suitable kind such that they are capable of recognizing part of a fusion protein, although in particular and exemplary embodiments the probes are antibodies. Other kinds of probes include proteins, DNA, RNA, peptides, and/or beads, for example.

In a specific yet exemplary embodiment, a substrate is coated with antibody, and one will generally incubate the substrate with a solution comprising antibody either overnight or for a specified period of hours, for example. The plate will then be washed to remove incompletely adsorbed material. Any remaining available surfaces of the substrate are then "coated" with a nonspecific protein that is antigenically neutral with regard to the test antisera. These include bovine serum albumin (BSA), casein, or solutions of milk powder, for example. The coating allows for blocking of nonspecific adsorption sites on the immobilizing surface and thus reduces the background caused by nonspecific binding of antisera onto the surface. After binding of the antibody to the substrate, coating with a non-reactive material to reduce background, and washing to remove unbound material, the substrate is contacted with the biological sample to be tested under conditions effective to allow immune complex (fusion protein/antibody) formation. Detection of the immune complex then requires a detectable secondary binding antibody directed to a second region of the fusion protein. The term "under conditions effective to allow immune complex (antigen/antibody) formation" means that the conditions preferably include diluting the sample with the fusion proteins and/or the antibodies with solutions such as BSA, bovine gamma globulin (BGG) or phosphate buffered saline (PBS)/Tween, for example. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps, the contacted surface is washed so as to remove non-complexed material. A preferred washing procedure includes washing with a solution such as PBS/Tween, or borate buffer, for example. Following the formation of specific immune complexes between the test sample and the originally bound material, and subsequent washing, the occurrence of even minute amounts of immune complexes may be determined.

V. Detection of Fusion Proteins

In specific aspects of the invention, a chromosomal translocation-derived fusion protein is detected, such as from a sample from an individual. In particular, the first probe/substrate complex is recognized generally upon recognition of the respective second part of the fusion protein by the second probe. Thus, in certain aspects the second probe or the binding thereof to the first probe/substrate complex, or both, is detected. In particular aspects, the second probe bound to the complex is detected.

Detection may be by any suitable methods so long as the second probe or its binding to the complex is detectable. In specific aspects, the detection is visible, such as with the human eye or a machine, or both. Detection methods include by light, radioactivity, color, beads, or a combination thereof. Detection may be quantifiable, in specific embodiments. In addition to detection of a particular fusion protein, the invention may be employed to detect a modification that occurs on the fusion protein, such as phosphorylation, glycosylation, farnesylation, acetylation, a mutation, or combinations thereof.

Detection of the fusion protein may be direct or indirect. For example, a label on the second probe may be bound by another molecule, and the other molecule itself is detected.

VI. Detection of Characteristics of Fusion Proteins

In particular embodiments of the invention, one or more characteristics of the fusion protein is detected by a first probe that binds a first region of the fusion protein and/or a second probe that binds a second region of the fusion protein. In a specific aspect, the probe recognizes a particular domain, mutation, and/or modification of the fusion protein, and in further specific aspects, the modification is one or more post-translational modifications, such as phosphorylation, acetylation, glycosylation, myristilation, farnesylation, alkylation, glutamylation, glycylation, isoprenylation, lypoylation, phosphopantetheinylation, sulfation, selenation, ubiquitination, citrullination, deimination, deamidation, and so forth.

In specific embodiments of the invention, the one or more characteristics of the fusion protein are the target, at least in part, of a therapy, such as a cancer therapy. In further specific embodiments, the particular presence or absence of the characteristic is informative whether or not the therapy is or may become a resistant therapy, including a cancer therapy that is a resistant cancer therapy.

VII. Detection of Activation of Fusion Proteins

In particular aspects of the invention, the methods detect the activation of a fusion protein. In further aspects, information gleaned from the status of fusion protein activation is employed in decisions regarding a therapy. In particular embodiments, the activation of a fusion protein is informative whether or not a cancer therapy is beneficial. In specific aspects, the status of activation of a fusion protein is determined following one or more treatments that target the characteristic associated with the activation. For example, a kinase inhibitor may be employed as the cancer therapy, and it is useful to monitor phosphorylation of the fusion protein by methods of the invention. In addition to phosphorylation, other types of modifications may activate a protein, including farnesylation, acetylation, and glycosylation, for example.

VIII. Samples Comprising the Fusion Protein

In particular embodiments, a sample known to comprise the fusion protein or suspected of comprising the fusion protein is subjected to a substrate comprising a first probe that is capable of recognizing a first part of said fusion protein. In specific aspects, the sample is from an individual, such as a mammal, and including a human. The sample may be of any kind such that it allows recognition of the fusion protein by the first probe. The sample may comprise whole cells or may be completely or substantially acellular. The sample may be from any tissue or source in an individual, although in specific embodiments the sample comprises cell lysate, blood, plasma, serum, cerebrospinal fluid, nipple aspirate, saliva, urine, feces, cheek scrapings, biopsy, and so forth.

Samples may be from any individual or even from a collection of samples. The individual may already have been diagnosed with cancer or may be suspected of having or developing cancer. The samples may be obtained by the individual using any suitable means, including syringe, scalpel, swab, and so forth.

IX. Identification and/or Monitoring of Disease and/or Patient Therapy

In certain embodiments of the invention, the present invention is employed to identify a disease in an individual, such as identify cancer in an individual, by detecting one or more fusion proteins indicative thereof. The invention may also be utilized for identifying an individual that is suitable for a particular therapy. For example, the identification of one or more particular fusion proteins may indicate that the individual is well-suited for a particular cancer therapy or is not well-suited for a particular cancer therapy. In certain aspects, the identification of a particular fusion protein comprises identification of a marker, such as one or more mutations and/or protein modifications, that indicate that the individual would be refractory to a particular therapy, such as be resistant to the therapy or be likely to develop resistance to the therapy. In certain aspects, the presence of the fusion protein is identified in a sample, although the fusion proteins in the complex may be removed from the antibody/substrate complex to be further subjected to characterization. For example, the fusion proteins may be detected in the sample, although further analysis of representative fusion proteins from the sample or from the complex may provide additional information, such as information that assists in determining or monitoring a therapy.

In additional aspects, the present invention is employed to monitor a therapy for a patient. For example, in some cases the individual may develop resistance to a cancer therapy, and the invention may be utilized to identify fusion proteins indicative of the development of resistance or the risk or susceptibility for the development of resistance.

X. Quantification of Fusion Protein

In particular aspects of the invention, fusion proteins generated from chromosomal translocation are quantified. In certain aspects, the quantification of the fusion proteins is informative regarding cancer or a therapy therefor. For example, the quantification may be informative whether or not a particular cancer therapy is successful. In some aspects, the quantification detects the fusion protein and/or activation thereof.

Quantification of the fusion proteins or activated fusion proteins may occur by any methods suitable in the art. Although in the related art protein fusions may be estimated based on an average of molecules per bead surface, in particular aspects of the invention, the fusion proteins or activated fusion proteins are quantified with a more accurate and representative method. In particular aspects, an index is identified that considers the different numbers of molecules upon different beads. When this is reflected as a percentage of positive beads (beads with molecules upon them), it is multiplied by how many molecules are present on each bead. In specific embodiments, this relationship is reflected in the following formula: percentage of positive beads (based on a detectable signal)×median number of molecules of beads that are positive (this may be referred to as antibody binding capacity (ABC))=number of molecules in the sample.

An increase in the number of fusion proteins or activated fusion proteins, a decrease in the number of fusion proteins or activated fusion proteins, or no significant change (such as no statistically significant change) in the number of fusion proteins or activated fusion proteins may be informative concerning the success of a cancer therapy. In particular aspects, an increase in the number of activated fusion proteins and/or no significant change in the number of activated fusion proteins indicates that a cancer therapy is ineffective and that an alternative cancer therapy should be utilized.

XI. Antibodies

In certain aspects of the invention, two or more antibodies directed to nonidentical regions of the chromosomal translocation-generated fusion protein may be produced. Exemplary antibody characteristics and uses are described herein below.

A. Use of Antibodies

In coating a substrate with antibody, one will generally incubate the substrate with a solution of the antibody, either overnight or for a specified period of hours. The substrate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder, for example. The coating allows for blocking of nonspecific adsorption sites on the immobilizing surface and thus reduces the background caused by nonspecific binding of antisera onto the surface.

The immunobinding methods also include methods for detecting and quantifying the amount of a fusion protein in a sample and the detection and quantification of any immune complexes formed during the binding process. Here, one would obtain a sample suspected of containing the fusion protein, contact the sample with an antibody against a first region of the fusion protein, and then detect and quantify the amount of immune complexes formed under the specific conditions.

In terms of antigen detection, the biological sample analyzed may be any sample that is suspected of comprising a fusion protein, such as, for example, a tissue section or specimen, a homogenized tissue extract, a cell, an organelle, separated and/or purified forms of any of the above antigen-containing compositions, or even any biological fluid that comes into contact with the cell or tissue, including blood, plasma, urine, cerebrospinal fluid and/or serum, for example.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any fusion proteins present. After this time, the substrate comprising the sample-antibody composition will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker on the second antibody, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

B. Antibody Characteristics and Production of Antibodies

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, □-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196, 265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60 61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging".

Many appropriate imaging agents are known in the art, as are methods for their attachment to antibodies (see, for e.g.) U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine-211, 14-carbon, 51chromium, 36chlorine, 57cobalt, 58cobalt, copper67, 152Eu, gallium67, 3hydrogen, iodine123, iodine125, iodine131, indium111, 59iron, 32phosphorus, rhenium186, rhenium188, 75selenium, 35sulphur, technicium99m and/or yttrium90. 125I is often being preferred for use in certain embodiments, and technicium99m and/or indium111 are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl2, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Exemplary Materials and Methods

The following materials and methods were employed in the invention, although modifications within the scope of the present invention may be made by one of skill in the art.

Plasma was collected from patients with CML being treated with Gleevec under IRB-approved protocol. Peripheral blood from 96 healthy individuals was also collected as control following informed consent according to institutional guidelines. Pre-treatment peripheral blood samples as well as 3 months, 6 months, and 12 months samples were collected when possible. All samples were collected in EDTA (ethylenediaminetetraacetic acid) tubes. Diagnosis of CML was established based on clinical finding, cytogenetics, FISH studies, and RT/PCR analysis.

Carboxylated polystyrene beads (Bangs Laboratories, Inc., Fishers, Ind.) were coated with antibodies for BCR protein as recommended per manufacturer, following manufacturer-published protocols. Samples, plasma or lysate were diluted 1:50 in PBS containing 5% BSA, denatured with 2% SDS at 96° C. for 4 minutes, and spun down at 13,000 rpm for 2 minutes at room temperature. The supernatant was incubated with conjugated beads at room temperature for 2 hours with constant mixing. The beads were then washed a total of three times with PBS/5% BSA and resuspended in 600 µl of the same solution. Each sample was then further subdivided into 3 aliquots as follows: one for total BCR/ABL; one for phospho-ABL (Thr 735); and one for phospho-ABL (Tyr 245). To each aliquot was added 5 µl of the appropriate antibody and incubated at room temperature for one hour. Beads were then washed 3 times with PBS/5% BSA and resuspended in 5% BSA in PBS. Ten µl of 1:1 PE labeled goat anti-rabbit antibody (mouse and human adsorbed) were added and incubated at room temperature for 30 minutes, washed 3 times in PBS containing 5% BSA and 2% sodium azide, and resuspended in 500 µl 5% BSA in PBS. Samples were analyzed using BD FACSCanto flow cytometery platform.

To quantify the signal, the QuantiBrite system (Becton Dickinson and Company; San Jose, Calif.) was used, allowing us to consistently determine the intensity of staining on the bead surface since we used a 1:1 PE labeling. To adjust for percentage of beads that are positive, the present inventors used the following formula: percent positive×molecules on surface of each bead=number of molecules/100 beads/10 µl of plasma. This unite is used as an arbitrary unite for these measurements. An equal number of beads was used in each assay.

Example 2

Specificity of the Assay

The specificity of the assay was studied in the present example. K-562 cell lysate was used as a positive control. Plasma from normal control demonstrated no significant signal and was used as background control. K-562 lysate as well as plasma from patients with CML showed a significant signal above the negative control (FIG. 1).

Figure 2:
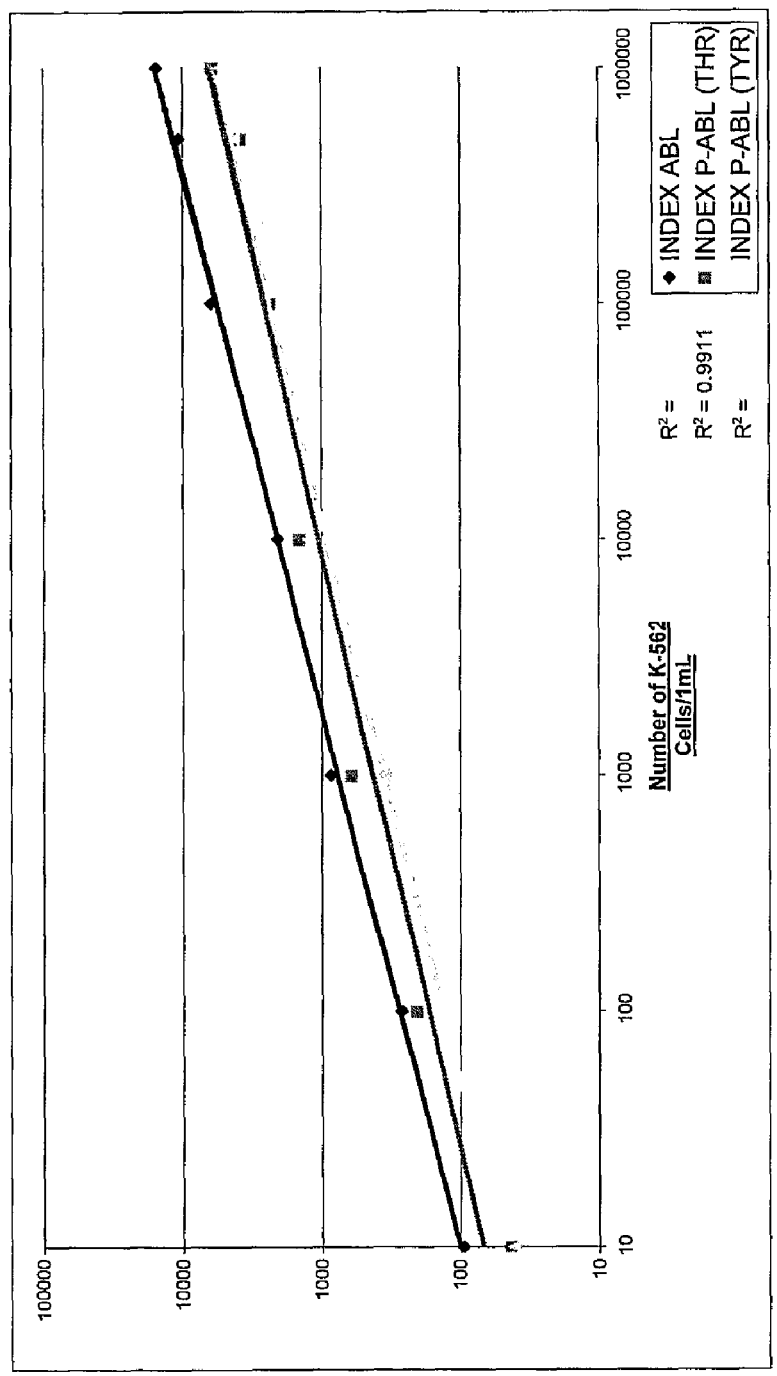
FIG. 2 demonstrates sensitivity and linearity of the bead-based assay for total and phosphorylated BCR-ABL protein. Cultured BCR-ABL positive K-562 cells were diluted in plasma obtained from normal subjects. The bead-based assay for BCR-ABL was performed as described in Example 1.

Ninety-six normal patient plasma samples were tested with all samples scoring negative, thus confirming specificity of the assay. In addition, 20 AML samples were tested and showed no significant signal past the normal negative control. To further determine the sensitivity of the assay, dilutions of K-562 cells in normal plasma were denatured to disperse cellular protein contents in the plasma and then analyzed. The sensitivity of the assay can be demonstrated up to 10 cells per milliliter of plasma (FIG. 2).

The CV of testing was 10% based on retesting 5 different times of various dilutions. To test stability of plasma samples, K-562 lysates diluted in plasma were stable up to 72 hours, and patient samples were also stable up to 72 hours (Table 1).

TABLE 1

CV Values from Demonstrating Stability

| Sample | Abl | p-Abl (Thr 735) | p-Abl (Tyr 245) | Ratio p-Abl (Thr):Abl | Ratio p-Abl (Tyr):Abl |
|---|---|---|---|---|---|
| Day 1 | 789182 | 219480 | 556068 | 0.28 | 0.70 |
| Day 2 | 813776 | 243950 | 395736 | 0.30 | 0.49 |
| Day 3 | 689216 | 193680 | 422606 | 0.28 | 0.61 |
| Day 4 | 728411 | 210864 | 480260 | 0.29 | 0.66 |
| Day 5 | 615614 | 210780 | 433657 | 0.34 | 0.70 |
| Avg | 727239.8 | 215750.80 | 457665.40 | 0.30 | 0.63 |
| Std | 79424.26 | 18335.84 | 62917.41 | 0.03 | 0.09 |
| CV % | 10.92 | 8.50 | 13.75 | 8.76 | 14.30 |

To test assay reproducibility and precision, the present inventors tested K-562 cell lysate from one culture in five different experiments. The Index values as well as ratios of phosphorylated to total BCR/ABL protein was examined. All CV values were below 10 percent indicating excellent precision for the assay. In addition stability of the assay was tested over 96 hours using K-562 lysate from one culture with identical criteria examined as for the precision study. Again the assay demonstrated excellent stability over time with CV values below 15 percent.

Example 3

Ex Vivo Monitoring Effects of Kinase Inhibitors

Figure 3:
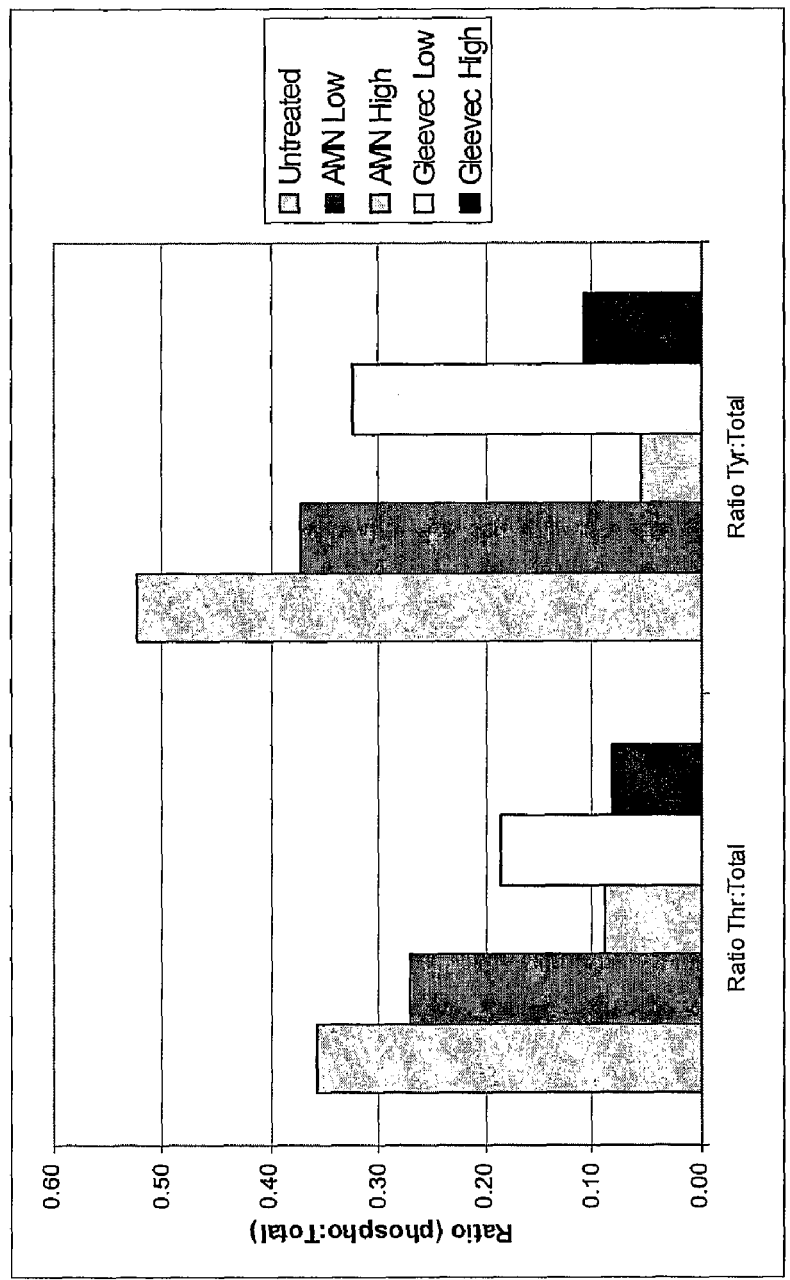
FIG. 3 provides summary results of the effects of exemplary kinase inhibitors (Gleevec and AMN107) on the BCR-ABL phosphorylation when incubated with K562 cell line.

Results from tissue culture drug treatment study indicate excellent clinical utility for monitoring of therapy (FIG. 3). Treatment at low dosage (0.5 µM) with the kinase inhibitor AMN107 (Novartis; Cambridge, Mass.) indicated a 1.32(Thr)- and 1.42(Tyr)-fold decrease from vehicle, while high dosage (5.0 µM) treatment demonstrated a 4.01(Thr)- and 9.30(Tyr)-fold decrease from vehicle, in all cases indicating reduction in activity resulting from treatment. Similarly, treatment with Gleevec indicated similar results with low dosage (0.5 µM) showing 1.91(Thr)- and 1.62(Tyr)-fold decreases, and high dosage (5.0 µM) resulting in a 4.32(Thr)- and 4.92(Tyr)-fold decrease from vehicle resultant of treatment. Cell lysates from K-562 cell line before and after treatment with Gleevec (0.5 and 5.0 µg) with a new kinase inhibitor (AMN107) showed significant reduction in BCR/ABL relative phosphorylation (Table 2).

TABLE 2

Fold Changes with Gleevec and Kinase Inhibitors

| Sample | Ratio Thr:Total | Fold decrease | Ratio Tyr:Total | Fold decrease |
|---|---|---|---|---|
| Vehicle | 0.36 | | 0.53 | |
| AMN Low | 0.27 | 1.32 | 0.37 | 1.42 |
| AMN High | 0.09 | 4.01 | 0.06 | 9.30 |
| Gleevec Low | 0.19 | 1.91 | 0.32 | 1.62 |
| Gleevec High | 0.08 | 4.32 | 0.11 | 4.92 |
| Normal | 0.00 | | 0.00 | |
| PBS | 0.00 | | 0.00 | |

Figure 4:
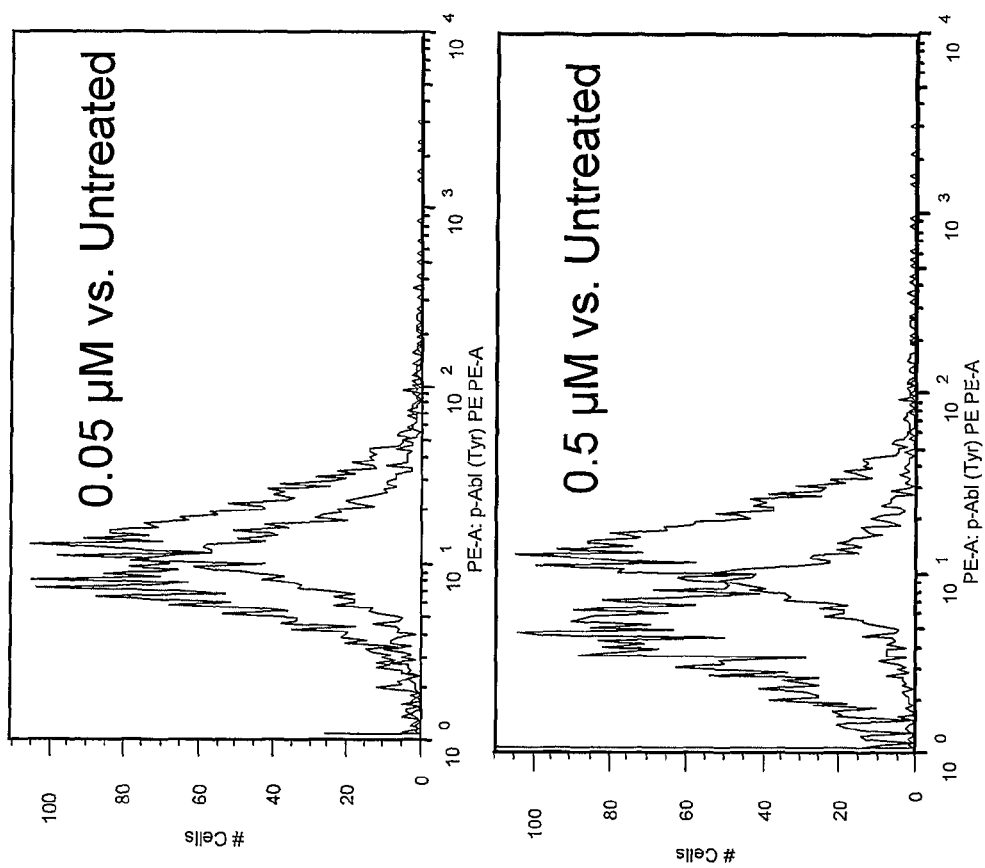
FIG. 4 shows reduction in amount of BCR-ABL protein phosphorylated on Tyr-245 after treatment of K-562 cells with AMN107. Flow cytometry results of the bead-based assay are shown for cultured K-562 cells treated with BCR-ABL-specific tyrosine kinase inhibitor AMN107 at the indicated concentrations (blue traces) or untreated control (black traces).

FIG. 4 shows an example of changes in Phospho BCR-Abl (Tyr) in lysate from K562 cells following treatment with AMN107.

Example 4

Monitoring Patients Treated with Therapy

Figure 5:
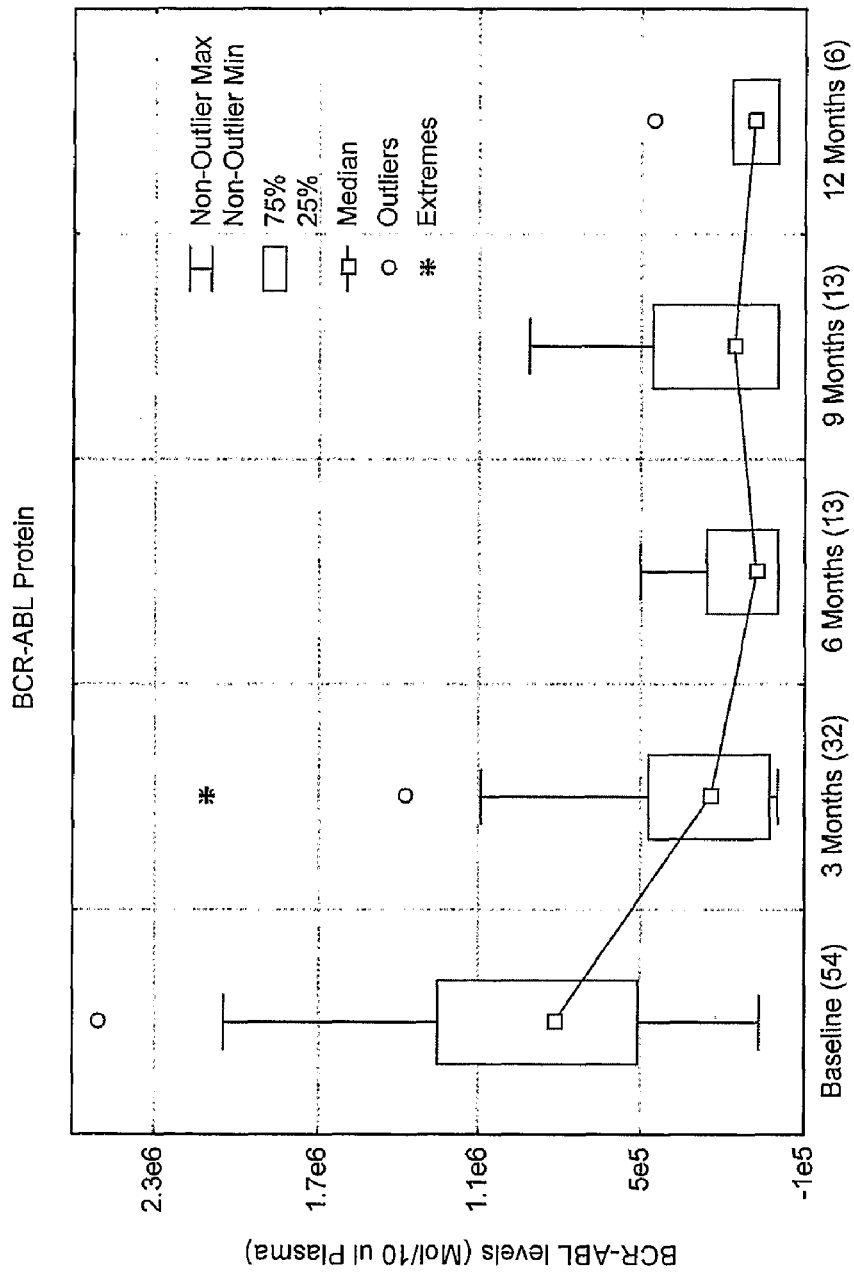
FIG. 5 demonstrates levels of total protein in CML patients before and during imatinib treatment. Plasma prepared from peripheral blood of CML patients was assayed by the bead-based method for total BCR-ABL protein.

Patients treated with Gleevec were tested before and while on the medication. As expected BCR/ABL protein was high at diagnosis and levels decreased significantly with therapy in a fashion parallel with that seen in Rt/PCR. Therefore BCR/ABL protein in plasma can be used as an alternative method to the PCR-based assay. FIG. 5 demonstrates changes in BCR-ABL protein levels in patients with CML on Gleevec.

The protein analysis has a CV of approximately 6%, in contrast to the CV in most PCR quantitative assays being greater than 20%. Therefore, the BCR/ABL protein assay in some embodiments of the invention is more reliable in detecting and monitoring minimal residual disease. Similarly, the present inventors measured the changes in the levels of the phosphorylated BCR-ABL, which showed a similar pattern.

Figure 6:
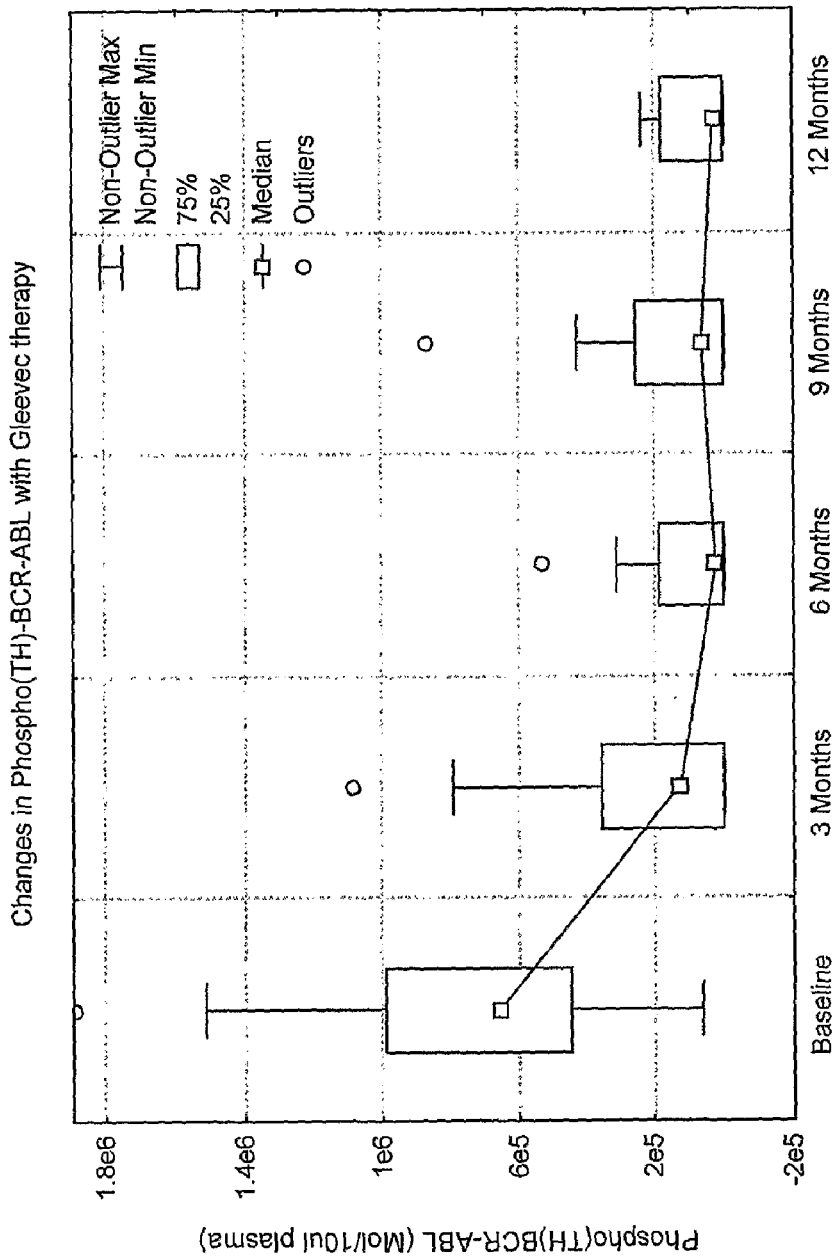
FIG. 6 shows levels of phosphorylated (Thr-735) BCR-ABL protein in CML patients before and during imatinib treatment. Plasma prepared from peripheral blood of CML patients was assayed by the bead-based method for phosphorylated (Thr-735) BCR-ABL protein.

FIG. 6 shows changes in Phospho(Tyr)-BCR-ABL protein levels in patients with CML on Gleevec.

Figure 7:
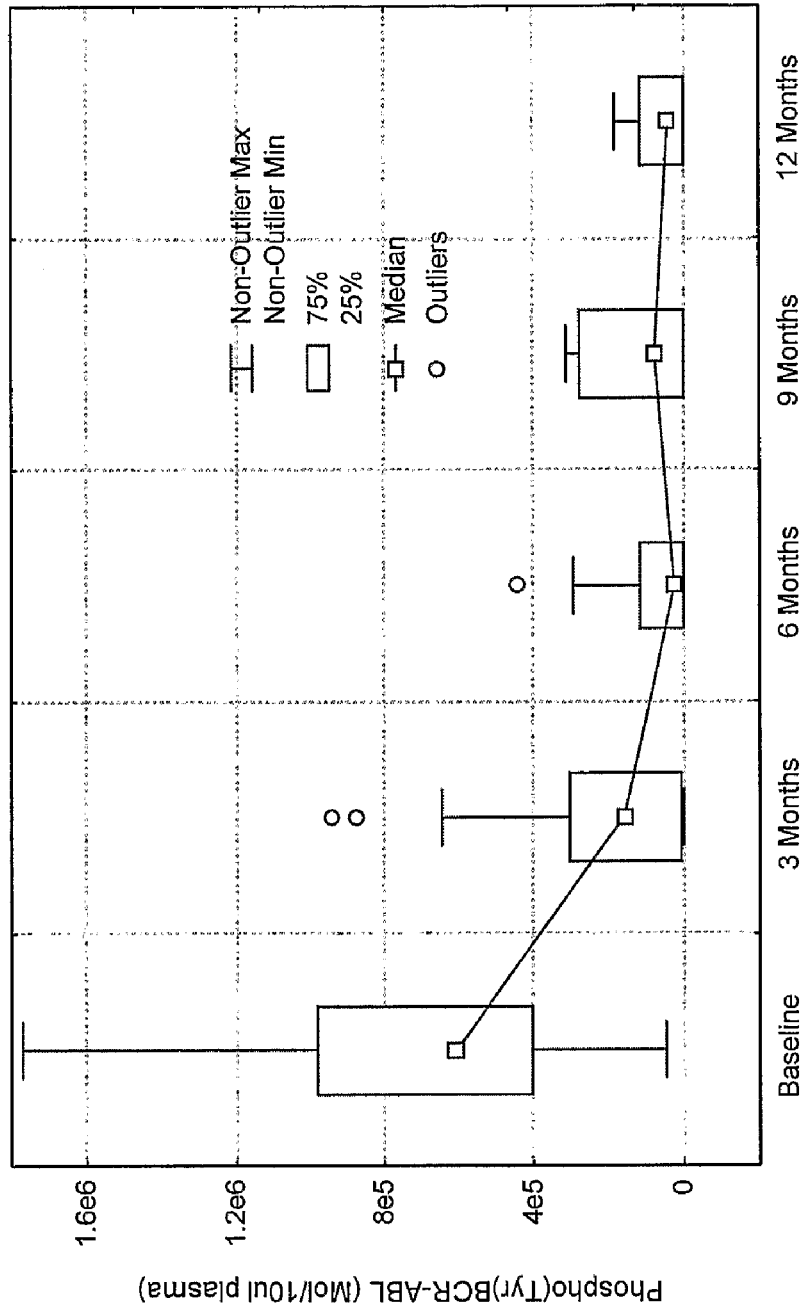
FIG. 7 shows levels of phosphorylated (Tyr-245) BCR-ABL protein in CML patients before and during imatinib treatment. Plasma prepared from peripheral blood of CML patients was assayed by the bead-based method for phosphorylated (Tyr-245) BCR-ABL protein.

Out of 33 samples analyzed at 3 months, 5 were negative by PCR using peripheral blood (PB) cells, all of which were positive by the protein assay as performed using the plasma (FIG. 7). There were 5 samples negative by BCR/ABL protein assay, and all were positive by PCR using PB cells. In contrast there were 32 samples collected at 6, 9, and 12 months of therapy. Of these patients 10 were negative by PCR using PB cells and 6 of these samples were negative by protein the protein assay as performed on plasma. Overall, there were 9 patients negative by plasma protein assay and of these 5 were negative by PCR as performed using PB cells. This data suggests that sensitivity of the two assays is similar at 6, 9, and 12 months of therapy on Gleevec.

Table 3 shows sensitivity of BCR-ABL protein assay in plasma as compared with RT-PCR assay using cells.

TABLE 3

Sensitivity of Protein Assay vs. RT-PCR

| | At 3 Months | | | At 6, 9, 12 months (32) | |
|---|---|---|---|---|---|
| | PCR+ | PCR− | | PCR+ | PCR− |
| P Protein, neg #5 | 5 | 0 | P Protein neg #9 | 4 | 5 |
| | Protein+ | Protein− | | Protein+ | Protein− |
| PCR neg #5 | 5 | 0 | PCR neg #10 | 4 | 6 |

Figure 8:
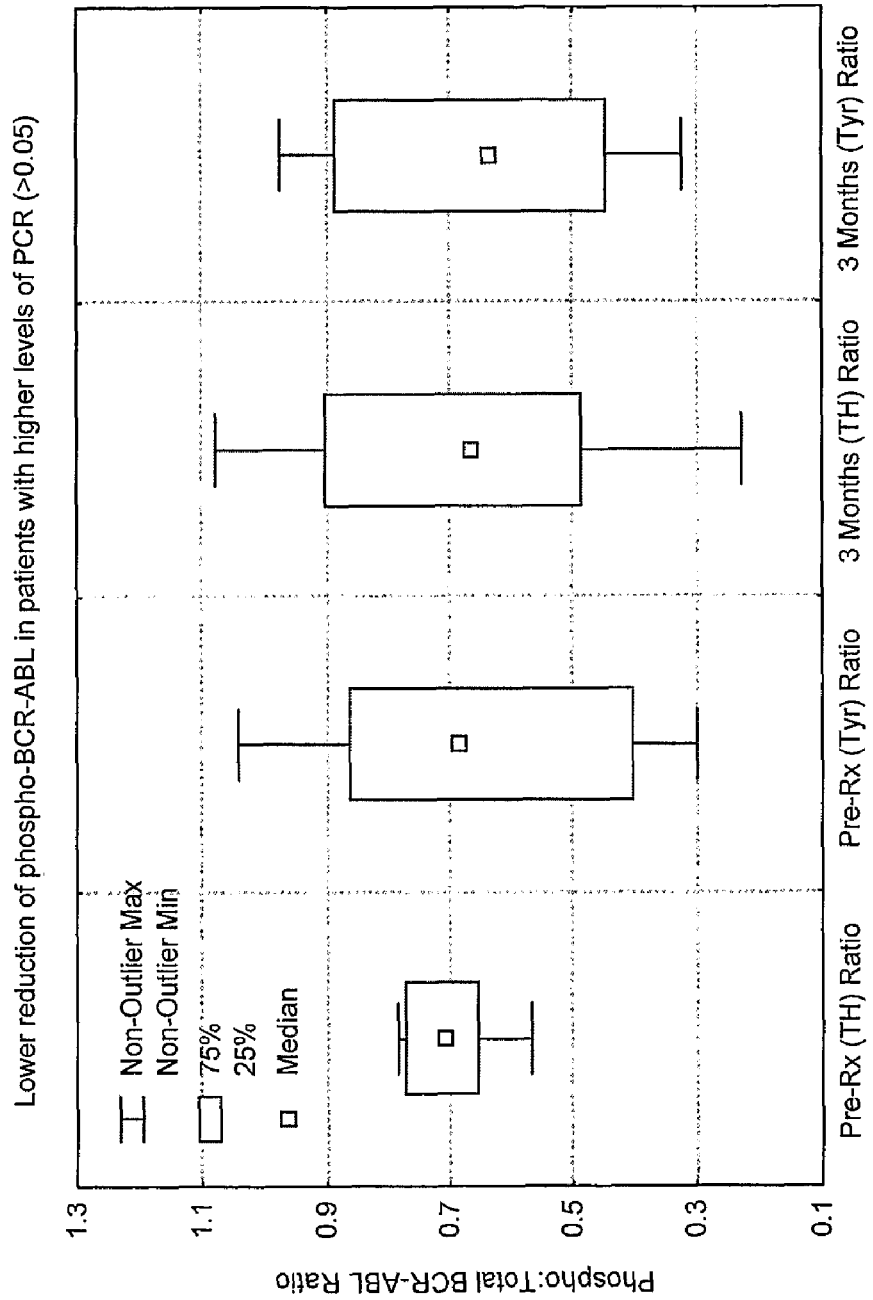
FIG. 8 demonstrates no significant decrease in levels of BCR-ABL phosphorylation in CML patients with poor molecular response to imatinib treatment. Poor molecular response was defined as a ratio of BCR-ABL to ABL mRNA of >0.05, as determined by RT-PCR after 3 months of treatment. The proportions of total BCR-ABL protein that were phosphorylated on Thr-735 (TH) and Tyr-245 (Tyr) are shown prior to and after 3 months of treatment for CML patients who did not show a molecular response

This protein analysis allows comparison of phosphorylation. Overall, BCR/ABL phosphorylation showed a similar pattern of reduction. However, when samples from patients treated with Gleevec, but had relatively higher level of disease by RT/PCR (>0.05 ratio of BCR-ABL:ABL mRNA) had no significant reduction of phosphorylation as compared to patients who had relatively low level of disease as determined by RT/PCR (<0.05 ratio of BCR-ABL:ABL mRNA). There is a lower reduction of phospho-BCR-ABL in patients with higher levels of PCR (>0.05). FIG. 8 demonstrates a lack of significant reduction in phosphorylation in poor responders (PCR>0.05) to Gleevec at 3 Months.

Figure 9:
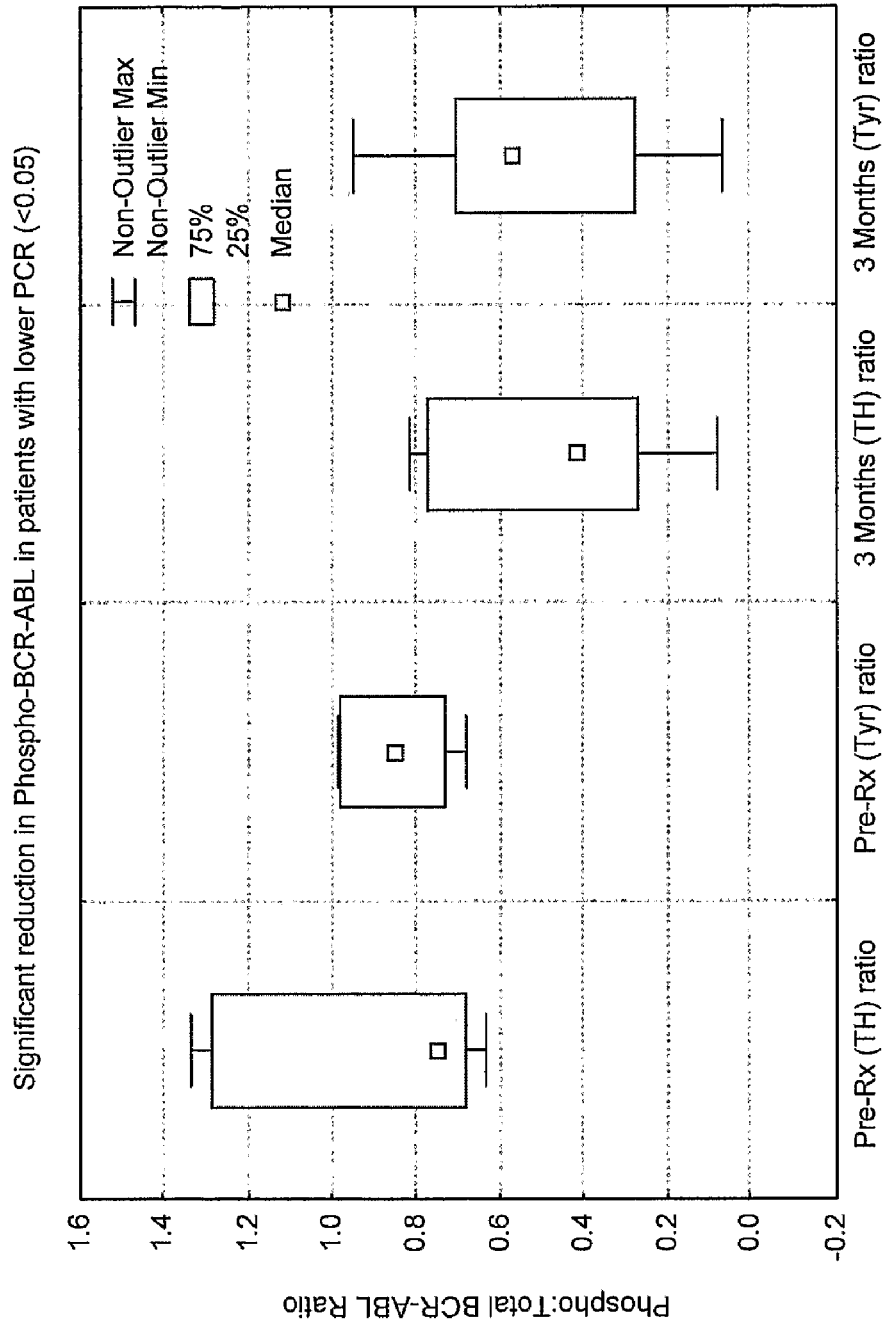
FIG. 9 shows decreased levels of BCR-ABL phosphorylation in CML patients with a molecular response to imatinib treatment. Molecular response was defined as a ratio of BCR-ABL to ABL mRNA of <0.05, as determined by RT-PCR after 3 months of treatment. The proportions of total BCR-ABL protein that were phosphorylated on Thr-735 (TH) and Tyr-245 (Tyr) are shown prior to and after 3 months of treatment for CML patients who did not show a molecular response.

FIG. 9 shows an association between good response (PCR<0.05) to Gleevec at 3 months with more significant reduction in phosphorylation (P=0.01). There is a significant reduction in phospho-BCR-ABL in patients with lower PCR (<0.05).

Figure 10:
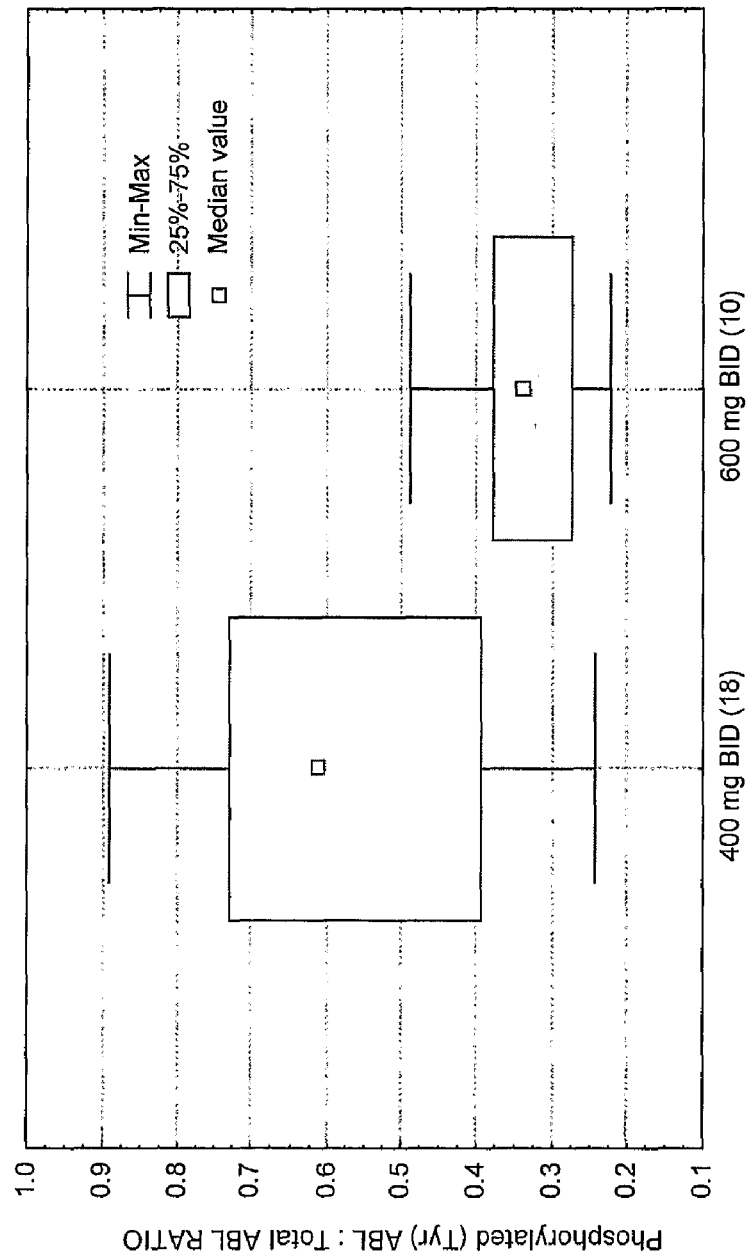
FIG. 10 shows more significant reduction in BCR-ABL phosphorylation when patients with CML are treated with 600 mg AMN 107 as compared with patients with 400 mg.

FIG. 10 shows more significant reduction in BCR-ABL phosphorylation when patients with CML are treated with 600 mg AMN107 as compared with patients with 400 mg.

FIG. 11 provides a table showing correlations between levels of BCR-Abl and its phosphorylation with various laboratory and clinical findings.

Example 5

Detection of Fusion Proteins Other than BCR-ABL

Although the previous examples concern the demonstration of the exemplary embodiment of BCR-ABL, the present invention may be utilized for the detection of any fusion protein. In some embodiments, the fusion protein is the result of a chromosomal translocation, whereas in alternative embodiments the fusion protein does not result from a chromosomal translocation. In embodiments wherein the fusion protein is the gene product resultant from a chromosomal translocation, any fusion protein from any chromosomal translocation may be detected so long as a first antibody to a first region recognizes the first region and a second antibody to a second region recognizes the second region, and the first and second regions are not identical. In specific embodiments, the fusion protein is a fusion of polypeptides encoded by a chimeric polynucleotide comprised of a first polynucleotide region from one gene and a second polynucleotide region from another gene, wherein both genes are those involved in the chromosomal translocation. In particular embodiments, a first antibody recognizes a polypeptide encoded by the first polynucleotide region and a second antibody recognizes a polypeptide encoded by the second polynucleotide region.

Example 6

Measuring Tumor Load

Figure 12:
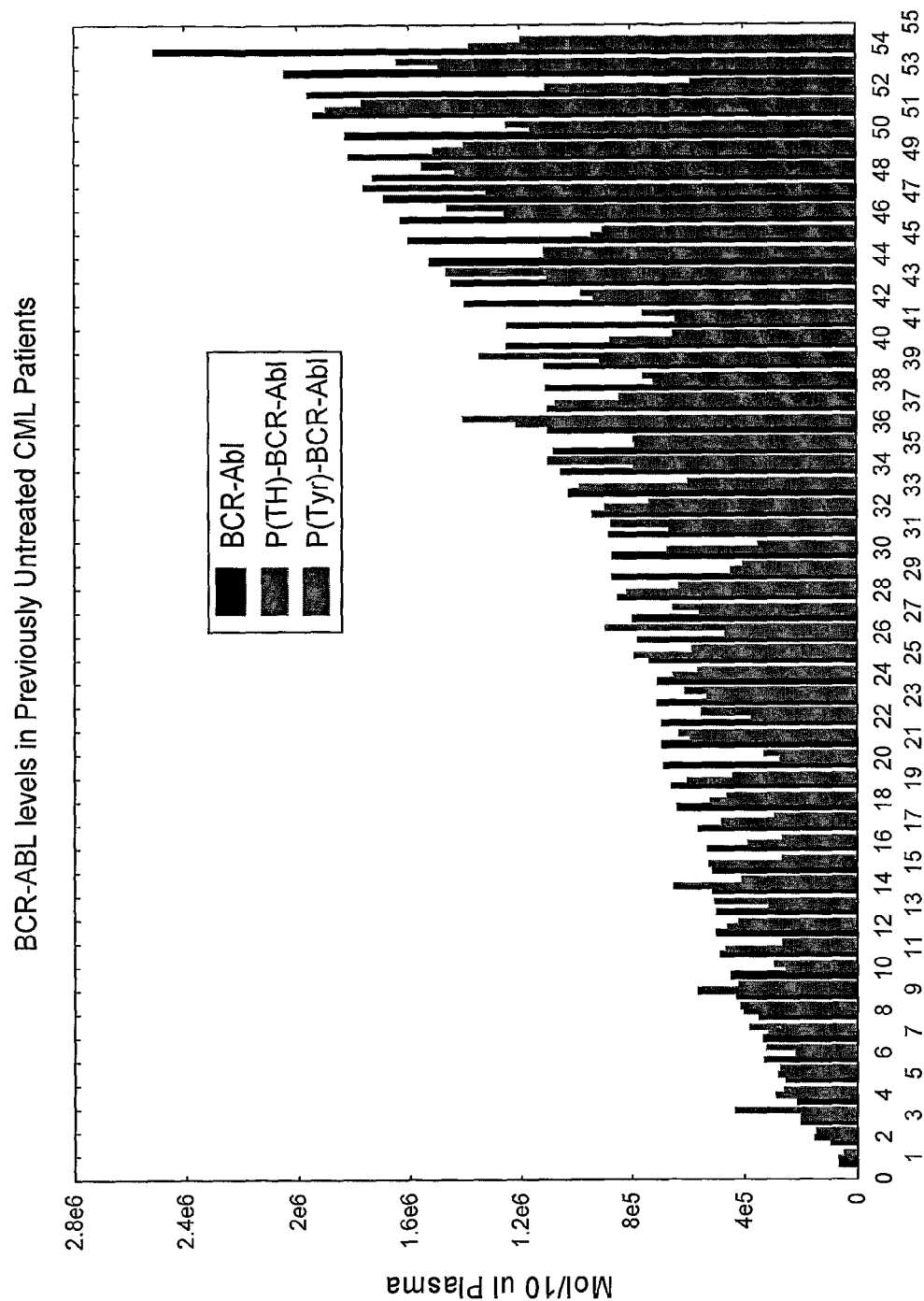
FIG. 12 illustrates measurement of tumor load related to BCR-ABL levels in untreated CML patients.

The present invention may be employed not only to monitor one or more characteristics of a fusion protein but additionally or alternatively the tumor load is measured. FIG. 12 demonstrates BCR-ABL levels in previously untreated CML patients, wherein the sample is obtained from plasma. The tumor volume in 54 exemplary CML patients is provided, with the levels of tumor mass arranged from lowest (patient #1) to highest (patient #54). The levels of phosphorylated fusion proteins are also shown, phosphorylated either at threonine or tyrosine. In specific embodiments of the invention, a cancer therapy is provided to these CML patients, and clinical response is measured thereafter. In particular embodiments, patients who have high tumor load need a higher dose of therapy as compared with patients with lower tumor load. Furthermore, the free protein in circulation binds the therapeutic agent and sequesters it from reaching cells and killing these cells, and this sequestration correlates with the levels of fusion protein in circulation (plasma/serum). In further specific embodiments, a method of the invention is employed to monitor the tumor load and/or fusion protein characteristics of at least some of these exemplary patients. In particular aspects, patients with cancer resistant to the therapy comprise low tumor volume but highly phosphorylated fusion protein.

Example 7

Exemplary Quantitation of Methods of the Invention

In some embodiments of the invention, quantitation of the fusion proteins is employed. This may be achieved by any suitable method of the invention, but in specific embodiments labeled probe binding to the fusion protein is measured by detecting a signal, such as fluorescence, associated with the probe. A suitable control may be used. The level of staining on the beads is determined by evaluating percentage of beads positive and median intensity of positivity on these beads. To encompass both parameter, the concept of INDEX was developed and is described pursuant to the exemplary PE/FITC labels.

The Index (molecule/100 beads)=(% of positive beads)× (median intensity)

The relative ratio of PE to FITC probe binding indicates the relative amount of fusion protein versus control in the sample.

One can determine from the percent of binding of the fusion protein versus the control form of the protein, the percentage of cells in a sample from the individual with the fusion protein. This can be done with the following formula.

$$\text{Actual \%} = (200X)/(X+Y)$$

X=number of chromosomal translocation-derived fusion proteins
Y=number of control proteins Using this formula is possible only when one fluorochrome is labeled to one fusion protein/antibody.

If one uses an independent protein as the control value to quantify the percentage of cells with the fusion protein, the formula is:

Actual %=2(Y–X)

Assuming:
X=chromosomal translocation-derived fusion proteins
Y=number of control proteins
Using this formula is possible only when one fluorochrome is labeled to one molecule of fusion protein/antibody.

Example 8

Levels of BCR-ABL Phosphorylation

CML cells from imatinib-resistant patients had significantly lower levels of both p-BCR-ABL (Thr735) and p-BCR-ABL (Tyr245) than CML cells from imatinib-naive patients. The mean ratio of p-BCR-ABL (Thr735) to total BCR-ABL was 0.69 (median, 0.64; range, 0.03-1.63) in resistant patients and 0.84 (median, 0.80; range, 0.40-1.67) in imatinib-naive patients (P<0.001; FIG. 13A), while the mean ratio of p-BCR-ABL (Tyr245) to total BCR-ABL was 0.71 (median, 0.71; range, 0.02-2.18) in resistant patients and 0.84 (median, 0.80; range, 0.30-2.15) in imatinib-naive patients (P=0.03; FIG. 13B). Thus, the level of BCR-ABL tyrosine activity paralleled the level of BCR threonine kinase activity in both cell populations, indicating that BCR-ABL tyrosine kinase was not being overexpressed in imatinib-resistant cells.

Example 9

Levels of CrkL, Akt, and Stat5 Phosphorylation

Figure 15:
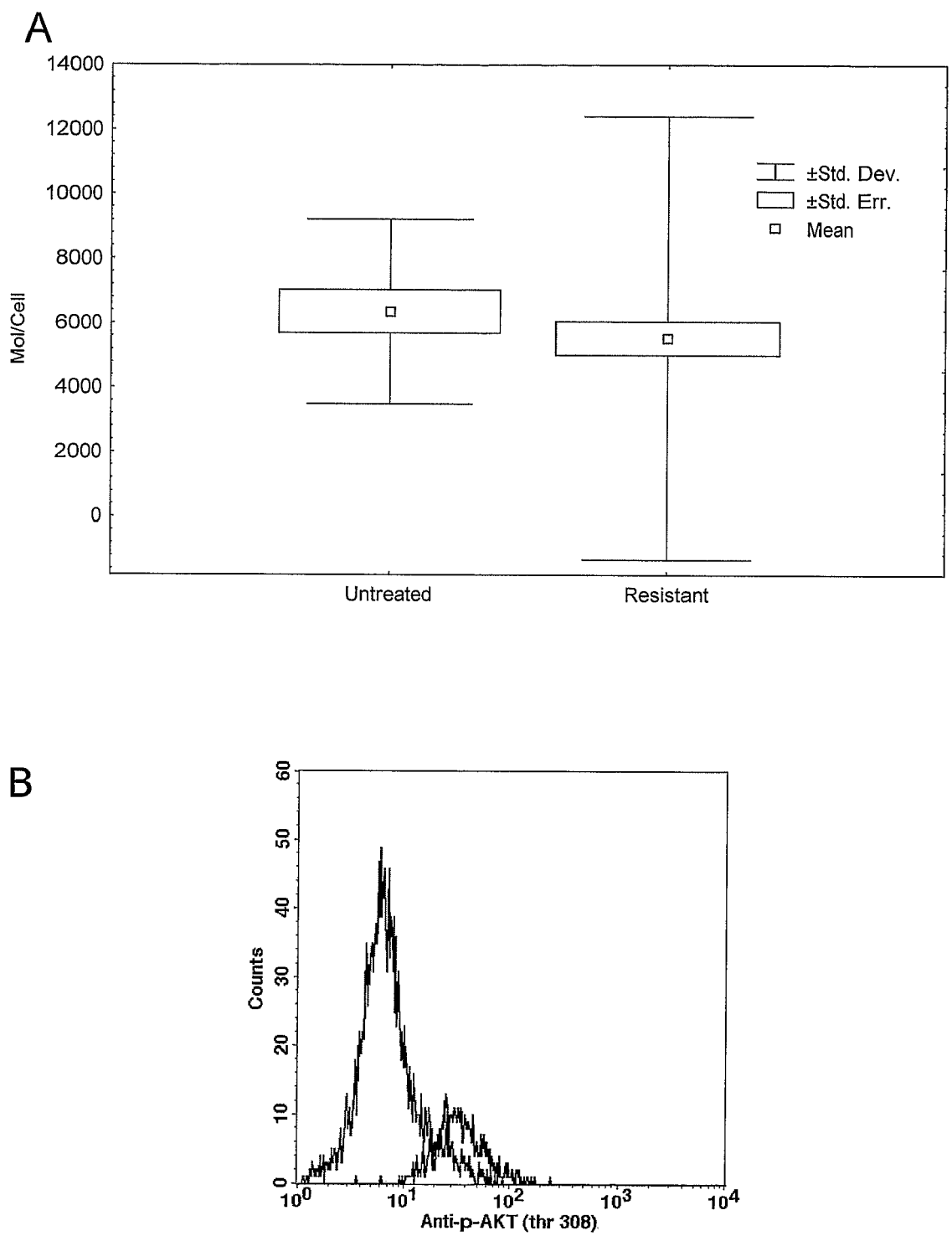
FIGS. 15A-15B show Akt phosphorylation in imatinib-naive and imatinib-resistant CML patients.

Compared with CML cells from imatinib-naive patients, CML cells from imatinib-resistant patients had significantly lower mean levels of p-CrkL (median, 4204 versus 5982 mol/cell, P=0.01; FIG. 14A) and p-Akt (median, 4131 versus 5949 mol/cell, P=0.008; FIG. 15A). This was observed despite an increase in the overall percentage of p-CrkL (FIG. 14B) and p-Akt (FIG. 15B)-*positive* cells in resistant patients attributable to an increase in blasts.

Mean p-STAT5 levels did not differ significantly between cells from the imatinib-naive patients and cells from the imatinib-resistant patients (FIG. 16A). The percentage of p-STAT5-positive cells, however, was significantly higher in the resistant patients (median 22% vs. 8%, P=0.02; FIG. 16B), indicating that the proliferation rate of STAT5 expressing cells was not determined by BCR-ABL kinase activity.

Many mechanisms of imatinib-resistance have been observed, and the most common is believed to be the restoration of BCR-ABL tyrosine kinase activity via decreased drug binding (Nardi et al., 2003). The first mutation reported to accomplish that was T315I (Gorre, 2001), and reports of many others followed. If imatinib binding failure is the key problem in resistance, drug design, in specific embodiments, should focus on more effective ways to block BCR-ABL tyrosine kinase activity. Exemplary data of the present invention, however, showed that the phosphorylation levels of BCR-ABL and its downstream targets CrkL and Akt were lower in imatinib-resistant patients than in imatinib-naive patients, indicating that imatinib resistance in the patient population was not the result of poor drug binding and reversion to high levels of BCR-ABL signaling. While binding site mutations undoubtedly confer a survival advantage, especially those that predate imatinib therapy, they are more likely to exist in a subpopulation of leukemic clones that are able to contribute to disease progression (Nardi, 2003).

The finding that STAT5 phosphorylation levels in imatinib-resistant and -naive patients did not significantly differ despite the demonstrated decreases in activity of known upstream signaling effectors in the resistant patient samples support the embodiment that resistance can be due to activation of pathways that deviate from the canonical BCR-ABL signaling cascade. The src-family kinases Lyn and Hck, which are activated by BCR-ABL, can also be expressed in imatinib-resistant CML cells with suppressed exhibit tyrosine kinase activity (Donato 2005). In specific embodiments of the invention, additional characterization of resistance is performed to examine specific mutations, the activation of alternative pathways, and the embodiment that one mechanism is associated with another.

Example 10

Significance of the Present Invention

The deregulated kinase activity of ABL protein in CML is believed to be the hallmark of this disease and responsible for proliferation and reduced apoptosis. A direct measure of both the BCR/ABL protein as well as its activity would be the most accurate measure of disease activity and progression. The specific activity of tyrosine kinase inhibitors targeting the BCR/ABL protein as therapy lends itself to a necessity for direct measure of the targeted protein activity. Yet, the unstable nature of the protein and its large size limit the ability to detect and measure activity via standard western blot analysis. Therefore, developing an assay that is rapid and practical in a clinical laboratory can be very helpful. Using immunoprecipitation on beads with minor denaturing appears to preserve the integrity of this large and complex protein. This kind of immunopercipitation most likely maintains the overall structure of the protein and perhaps keeps the protein in its complexed form, therefore maintaining its integrity and phosphorylation. The data presented here indicates that this approach is amenable to analysis even as a plasma protein. The present inventors have previously demonstrated that leukemic cells release their proteins, DNA, and RNA into plasma. Here, the present inventors used plasma for detecting BCR/ABL fusion protein and its phosphorylation. The use of patient plasma as a sample type to detect circulating BCR/ABL protein allows for an accurate and sensitive measure of overall leukemic activity without dependance on sampling.

The data presented herein demonstrates that BCR/ABL is in fact detectable at significant levels within circulation in patient plasma. By using a bead-based ELISA assay, the present inventors are able to initially immunoprecipitate the BCR and BCR/ABL and further detect translocation through the use of an ABL-specific antibody. Activation of the protein was detected using antibodies against phosphorylation at two specific residues. The specificity of the assay is validated using 96 normal patient plasma samples all testing negative for the translocation, as well as both K-562 and CML patient plasma that were used as positive controls for the assay. The variations observed within circulating levels of BCR/ABL among patients with CML is most likely indicative of tumor mass, proliferation rate, as well as cellular turnover into the plasma, in specific embodiments.

The direct correlation between a decrease in BCR/ABL phosphorylation and drug treatment indicates the clinical utility of the assay to detect and measure activity resultant from treatment. In addition, the direct correlation between RT-PCR levels and response, as a measure of activity, indicates that phosphorylated-to-total BCR/ABL ratios can be used as a diagnostic tool for response. Patients with a higher ratio of phosphorylated-to-total protein showed higher RT-PCR values after three month treatment with Gleevec, indicative of poorer response to the kinase inhibitory function of therapy. In addition, the assay indicated that there was reduction in total as well as activated levels of BCR/ABL protein in response to therapy as compared to baseline levels, with significant correlation to RT-PCR levels. In short, measurement of total as well as phosphorylated BCR/ABL levels via the bead-based assay proved a simple and reliable diagnostic tool as well as a more comprehensive measure for monitoring therapy. In specific embodiments, this approach replaces PCR-based assays that are difficult to standardize and quantify.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents and Patent Applications

U.S. Pat. No. 3,996,345
U.S. Pat. No. 4,062,733
U.S. Pat. No. 4,366,241
U.S. Pat. No. 4,104,029
U.S. Pat. No. 5,369,008
U.S. Pat. No. 6,686,165
W 95/15331

Publications

Ahuja, H. G. et al. Blood, 94 (9); 1999; pp. 3258-3261.
Arai, Y., et al. Blood 89; 1997; pp. 3936-3944.
Borrow, J. et al. Nat. Genet. 12; 1996; pp. 159-167.
Dai Y, et al. J Biol Chem. 2004 Aug. 13; 279(33):34227-39.
Donato et al., ASH Annual Meeting Abstracts, 2005, 106: Abstract 1087
Donato et al. Blood. 2003 Jan. 15; 101(2):690-8.
Donato et al. Cancer Res. 2004 Jan. 15; 64(2):672-7.
Gorre et al. Science. 2001; 293:876-880
Nakamura, T. et al. Nat. Genet. 12; 1996; pp. 154-158.
Nardi V, et al. Curr Opin Hematol. 2003; 11(1):35-43.
Raza-Egilmez, S. Z. et al. Cancer Res. 58; 1998; pp. 4269-4273.
Talpaz, M. et al. Leukemia 14(9); 2000; pp. 1661-1666.
Valk, P. et al., "Molecular Diagnostics of Hematopoietic Diseases"; www.eur.nl/fgg/hema/nederlands/onderzoek/overige.html Aug. 27, 2003.
van Denderen, J. et al. Blood 76; 1990; pp. 136-141.
Wallace, J. et al. Leukemia 17(7); 2003; pp. 1404-1410.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of determining the tumor load of an individual having chronic myeloid leukemia (CML) characterized by a chromosomal translocation that produces a fusion protein comprised of a first and second region and that is phosphorylated, said method comprising the step of quantifying the amount of the phosphorylated fusion protein in a plasma or serum sample from the individual, wherein said amount correlates with tumor load to thereby determine the tumor load of the individual, wherein the fusion protein is BCR-ABL.

2. The method of claim 1, wherein the quantifying step comprises:
    subjecting the sample to a first probe that is present on a surface and that is capable of binding said first region of the fusion protein, wherein binding of the first probe to the first region produces a first probe/fusion complex;
    subjecting the first probe/fusion complex to a second probe, wherein the second probe is capable of binding said second region of the fusion protein, and detects the phosphorylation of the fusion protein, wherein binding of the second probe to the second region produces a second probe/fusion protein complex; and
    quantifying the amount of phosphorylated BCR-Abl fusion protein in the second probe/fusion protein complex, thereby determining the tumor load.

3. The method of claim 2, wherein at least one of the probes is labeled.

4. The method of claim 3, wherein the label is selected from the group consisting of radioisotope, enzyme, fluorogen, chromogen, and chemiluminescent.

5. The method of claim 3, wherein the method is further defined as follows:
    a) the second probe is labeled and there is a 1:1 ratio of label to second probe for the second labeled probe; and
    b) the surface is further defined as a bead, and the quantifying is further defined as determining the product of the percentage of positive beads and the median number of molecules on the beads, said median number identified by the intensity of signal from the label.

6. The method of claim 2, wherein the at least one probe comprises an antibody.

7. The method of claim 6, wherein the antibody is labeled.

8. The method of claim 1, wherein the quantifying is further defined as measuring the ratio of phosphorylated fusion protein to total fusion protein.

9. The method of claim 1, wherein the determining of the tumor load is indicative of prognosis of the CML and/or responsiveness of a therapy for the CML.

10. The method of claim 9, wherein the determining of the tumor load occurs prior to and/or following the therapy.

11. The method of claim 9, wherein the therapy targets the phosphorylated fusion protein.

12. The method of claim 9, wherein the therapy comprises a kinase inhibitor, an antibody, or a cytotoxic drug.

13. The method of claim 12, wherein the kinase inhibitor is selected from the group consisting of STI571 and AMN107.

14. The method of claim 1, wherein the determining of the tumor load is indicative of responsiveness of a therapy for the CML and wherein a higher ratio indicates the individual has responded poorly to the therapy or will respond poorly to the therapy.

15. The method of claim 14, wherein the therapy comprises a kinase inhibitor, an antibody, or a cytotoxic drug.

16. The method of claim 15, wherein the kinase inhibitor is selected from the group consisting of STI571 and AMN107.

17. The method of claim 1, wherein the sample is a plasma sample.

18. The method of claim 1, wherein the sample is a serum sample.

\* \* \* \* \*